(12) United States Patent
Gao et al.

(10) Patent No.: US 6,303,011 B1
(45) Date of Patent: Oct. 16, 2001

(54) GAS SENSOR

(75) Inventors: Yunzhi Gao; Yukio Nakanouchi; Akira Kunimoto; Masaharu Hasei; Yongtie Yan; Takashi Ono, all of Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/099,401

(22) Filed: Jun. 18, 1998

(30) Foreign Application Priority Data

| Jun. 23, 1997 | (JP) | 9-180247 |
| Jun. 30, 1997 | (JP) | 9-187149 |
| Jul. 2, 1997 | (JP) | 9-190751 |

(51) Int. Cl.$^7$ .................................................. G01N 27/407
(52) U.S. Cl. ......................... 204/425; 204/426; 204/427; 205/781
(58) Field of Search .................................. 204/426, 424, 204/425, 427; 205/781

(56) References Cited

U.S. PATENT DOCUMENTS

| 4,199,425 | | 4/1980 | Sinkevitch | 204/195 |
| 4,840,913 | * | 6/1989 | Logothetis et al. | 204/424 |
| 5,217,588 | * | 6/1993 | Wang et al. | 204/153.1 |
| 5,242,573 | * | 9/1993 | Hayakawa et al. | 204/426 |
| 5,380,424 | * | 1/1995 | Friese et al. | 204/424 |
| 5,763,763 | * | 6/1998 | Kato et al. | 204/426 |
| 5,861,092 | * | 1/1999 | Kiyota et al. | 205/781 |
| 5,866,799 | * | 2/1999 | Kato et al. | 73/31.05 |
| 5,879,526 | * | 3/1999 | Dietz et al. | 204/426 |
| 5,893,968 | * | 4/1999 | Kato | 205/784.5 |
| 5,897,759 | * | 4/1999 | Kurosawa et al. | 204/424 |
| 5,902,469 | * | 5/1999 | Kato et al. | 204/425 |

FOREIGN PATENT DOCUMENTS

| 59-91358 | 5/1984 | (JP) . |
| 4-142455 | 5/1992 | (JP) . |
| 6-123726 | 5/1994 | (JP) . |
| 8-271476 | 10/1996 | (JP) . |
| 9-274011 | 10/1997 | (JP) . |

OTHER PUBLICATIONS

Nobuhide Kato et al., "Thick film $ZrO_2$ $NO_x$ Sensor", SAE Technical Papers 960334.

* cited by examiner

Primary Examiner—Robert J. Warden, Sr.
Assistant Examiner—Kaj K. Olsen
(74) Attorney, Agent, or Firm—Kubovcik & Kubovcik

(57) ABSTRACT

A nitrogen oxide sensor includes a solid electrolytic substrate exhibiting oxygen ion conductivity, a noble-metal reference electrode, which is active only to oxygen, formed on one side of the solid electrolytic substrate, and a sensing electrode, which is active to NOx and oxygen, formed on the opposite side of the solid electrolytic substrate. A potential difference across the sensing electrode and the reference electrode is output as a signal indicative of NOx concentration. Nitrogen oxides in a gas to be examined or measured gas are converted to $NO_2$ and to peroxides of nitrogen such as $N_2O_5$ and $NO_3$, after which the nitrogen oxides in the gas to be examined or measured gas are sensed by the sensing electrode as the peroxides of nitrogen such as $N_2O_5$ and $NO_3$ or as a mixed gas of $NO_2$ and the peroxides of nitrogen.

13 Claims, 16 Drawing Sheets

CONNECTED TO
VOLTAGE
MEASUREMENT
CIRCUIT

CONNECTED TO
POTENTIOSTAT

--☐-- CONVERSION VOLTAGE 0.4 V
--◇-- CONVERSION VOLTAGE 1.0 V
—○— CONVERSION VOLTAGE 0.8 V

GAS SENSOR

BACKGROUND OF THE INVENTION

1. Field of the Invention

This invention relates to a gas sensor and, more particularly, to an NOx sensor for sensing the concentration of nitrogen oxides contained in combustion gas or in exhaust gas from an internal combustion engine. The invention further relates to a solid-state sensor for sensing NOx gases, the sensor being suited to the sensing of NOx exhausted from combustion devices in general and NOx contained in automotive exhaust gas subjected to high temperatures in particular.

2. Description of the Related Art

An NOx sensor typical of the solid-state type disclosed thus far is described in the specification of Japanese Patent Laid-Open Publication No. 4-142455. This sensor includes a nitrate electrode and a reference electrode provided on an ion conductor residing in the sensed environment and measures an electromotive force produced across the electrodes. Though this sensor is sensitive to both NO and $NO_2$, the sensitivities to NO and $NO_2$ differ. As a consequence, the concentration of total NOx cannot be detected in a measurement environment in which both gases coexist and it is not possible to detect the concentration of NO or $NO_2$ separately.

In an effort to improve the sensitivities to NO and $NO_2$, there has been disclosed an emf-type sensor in which an auxiliary electrode is coated or mixed with an NO oxidizing catalyst. (See the specification of Japanese Patent Laid-Open Publication No. 6-123726.) In accordance with this proposal, NO contained in a gas in which NO and $NO_2$ coexist is oxidized to $NO_2$ so that a single component gas can be obtained. This makes it possible to detect the total NOx concentration. However, the accuracy of this method is decided by the oxidizing ability of the catalyst, just as with the conventional method of analysis, and a value different from the actual NOx concentration may be obtained. Further, since sensors of this type use a nitrate for the auxiliary electrode, problems arise in terms of resistance to humidity and heat. Difficulties in terms of long-term stability make it nearly impossible to put these sensors to practical use.

A sensor utilizing the semiconductor properties of various oxides to measure a change in electrical conductivity based upon the concentration of NOx has also been reported. However, since the sensitivity to NO and the sensitivity to $NO_2$ differ in this sensor as well, the concentration of NOx in a measurement environment in which NO and NOx coexist cannot be sensed.

A recently proposed method electrolyzes NOx gas electrochemically and senses NOx concentration based upon the value of electrolytic oxygen ion current. (See SAE Technical Paper 960334 or the specification of Japanese Patent Laid-Open Publication No. 8-271476.) The detection principle of this sensor is itself based upon that of electrolytic current-type sensors used widely heretofore to sense other gases.

Specifically, this sensor has an ion conductor provided internally with two chambers. In the first chamber oxygen is drawn out by an oxygen pump to make the concentration of oxygen in the measurement environment substantially zero and reduce $NO_2$ to NO. A voltage is applied to electrodes provided in the second chamber to ionize oxygen produced by the reduction to NO in the measurement environment. The resulting electrolytic current is then detected to sense the concentration of NOx. The NOx concentration sensed by this sensor varies greatly depending upon the performance of the oxygen pump. Further, in a case where the concentration of gas to be sensed is low, the concentration of residual oxygen in the measurement environment interferes with measurement. Moreover, since the signal current is extremely small, the S/N ratio is degraded in a noisy environment, such as in an automobile. This makes it difficult to detect NOx concentration accurately.

The inventors have proposed an emf-type NOx sensor and filed for patents. Though these proposals provide good sensitivity to NO or $NO_2$ gas, there are instances where the NO and $NO_2$ gases interfere with each other or are susceptible to interference from the reducing gas.

The inventors have further proposed (Japanese Patent Application No. 8-85419) a sensor not susceptible to interference from a reducing gas. This sensor includes an oxygen pump and an NOx sensing electrode formed on a solid electrolyte. When a reducing gas is oxidized, Nox gas is oxidized to $NO_2$ gas at the same time, thereby suppressing interference. However, this arrangement does not necessarily provide a solution to the problem of mutual interference between the NO and $NO_2$.

A noble-metal electrode is expected to serve as an excellent sensing electrode because it exhibits satisfactory resistance to heat even in a high-temperature environment such as automotive exhaust gas. In this respect a platinum sensor is in use as a $\lambda$ sensor or air-fuel ratio sensor in automotive vehicles and has demonstrated high reliability in actual use. Other advantages expected of noble-metal electrodes are chemical stability, ease of manufacture and low impedance. Examples of NOx gas sensors using a noble-metal sensing electrode on a solid electrolytic substrate of zirconia are referred to in the specification of Japanese Patent Laid-Open Publication No. 8-271476. These will now be described.

The first is set forth in the specification of U.S. Pat. No. 4,199,425. This specification discloses a sensor obtained by providing an automotive oxygen sensor ($\lambda$ sensor) of the concentration cell type with an alumina overcoat layer impregnated with rhodium in order to furnish NOx sensitivity. However, it is obvious that the rhodium-impregnated overcoat layer in this structure functions as an NOx decomposing catalyst layer and that oxygen produced by the decomposition of NOx is itself sensed by a platinum sensing electrode.

The second example is disclosed in the specification of Japanese Patent Laid-Open Publication No. 59-91358. This sensor includes a solid electrolytic substrate of zirconia, an electrode comprising a noble metal such as platinum, rhodium, palladium or gold formed on the substrate, and a sensing electrode formed on the substrate and obtained by building up or supporting an $N_2O$ decomposing catalyst such as $CO_3O_4$ on the electrode. A potential difference across these electrodes is measured. When measurement of NOx in automotive exhaust gas is considered, the gases of interest are NO and $NO_2$ and measurement of $N_2O$ is not performed Furthermore, the potential difference with respect to gases of low concentration is extremely low and there is almost no potential difference in the intermediate concentration region (less than several thousand ppm) of actual exhaust gas.

Thus, even if a sensing electrode made of noble metal is used in a concentration cell type NOx sensor according to the prior art, the function of the electrode is merely that of an NOx decomposing catalyst and the electrode merely acts as a collector that collects electric charge involved in the electrolytic reaction with the catalyst layer. Further, as set forth also in the specification of Japanese Patent Laid-Open Publication No. 8-271476, the conventional NOx sensor using a sensing electrode of noble metal develops only a small potential and is highly dependent upon the concentration of oxygen in the environment of the sensed gas. The state of the art is such that these sensors can be applied only in a direction that decomposes NOx.

The electrode potential of a sensing electrode decided by NOx and $O_2$, namely the nitrogen-oxide sensitivity of a mixed potential-type NOx sensor that outputs an electromotive force with respect to a counter electrode, is influenced by the conversion efficiency of a gas equilibrium reaction between NO and $NO_2$ and the conversion efficiency of the electrode reaction, as a result of which the output signal of the sensor electrode is unsatisfactory. Accordingly, a sensor having a higher sensitivity is sought. When emf is detected, the reference electrode potential varies greatly depending upon the type of gas that takes parts in the electrode reaction. In addition, the concentration of the gas that takes part in the electrode reaction has a major influence upon the emf of the sensor electrode. As is well known, the equilibrium between NO and $NO_2$ shifts in the direction of NO as temperature rises, and $NO_2$ obtained by a change brought on by the electrode reaction decomposes into NO. This causes a decline in emf when $NO_2$ is sensed. However, if nitrogen oxide in a gas to be sensed is oxidized to a peroxide of nitrogen of order greater than $NO_2$, the standard equilibrium potential of the peroxidized nitrogen oxide rises and it is possible to achieve a sensitivity in excess of the emf obtained with $NO_2$ gas. Furthermore, if the concentration of oxygen in the environment surrounding the sensing electrode is raised, advantages are gained in terms of producing the peroxidized nitrogen oxide and it is believed that the reaction through which $NO_2$ is decomposed into NO can be suppressed.

SUMMARY OF THE INVENTION

An object of the present invention is to raise the emf of a sensing electrode by utilizing an electrode reaction to oxidize nitrogen oxide in a gas to be examined or measured gas to $NO_2$ and peroxides of nitrogen of order greater than $NO_2$ to the greatest extent possible.

Another object of the present invention is to provide a total nitrogen oxide sensor in which maximum emf and sensitivity can be obtained by pumping excess oxygen into a measurement chamber and rapidly sensing peroxides of nitrogen thus obtained.

Among the gases of nitrogen oxide, NO gas and $NO_2$ gas exhibit significantly different gas response characteristics, as a result of which these gases interfere with each other in an environment in which they coexist. In addition, nitrogen oxide gas is susceptible to interference from a reducing gas such as a hydrocarbon gas or CO gas. There is need for a nitrogen oxide sensor arrangement that can solve these problems simultaneously, namely a sensor having a large NOx output sensitivity and a high dependence on NOx concentration, wherein NOx concentration can be sensed accurately even in a noisy environment such as found in an automotive vehicle. Accordingly, a further object of the invention is to provide a sensor that satisfies these needs.

Though the potential-difference type Nox sensor using an oxide electrode provides a high sensitivity, as mentioned above, the sensor electrode resistance is high and a collector therefore must be formed in the sensing electrode. This reduces the electrode surface area.

On the other hand, a noble-metal electrode, which is an excellent electrical conductor, that measures an NOx potential difference per se is not to be found. The only such electrode available has some sensitivity in $N_2O$ (laughing gas). Moreover, with a noble-metal electrode, the potential difference itself is dependent upon the partial pressure of oxygen. This makes necessary the accurate control of oxygen concentration. In view of these problems, another object of the present invention is to provide a potential-difference NOx sensor having a noble-metal electrode exhibiting a low sensor impedance and excellent electrode conductivity, the sensor also exhibiting an outstanding NOx sensitivity characteristic.

Yet another object of the present invention is to provide a sensor which, even when applied to the exhaust gas of an automotive vehicle, will measure the NOx concentration without being influenced by the partial pressure of oxygen in the environment.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

The most basic embodiment of an NOx sensor according to the present invention will now be described.

Figure 1:
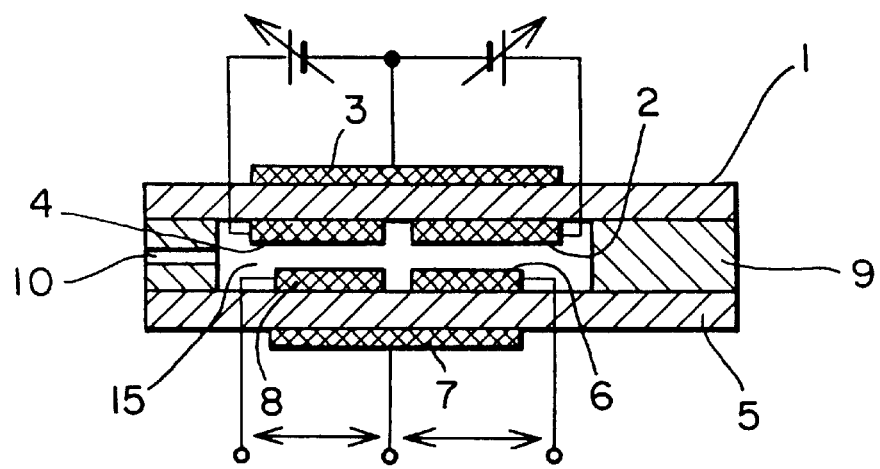
FIG. 1 is a sectional view illustrating a sensor according to an embodiment of the present invention.

FIG. 1 illustrates the basic components of a NOx sensor according to the present invention. A noble-metal electrode, a noble-metal electrode modified by another metal, a noble-metal alloy electrode, a metal-compound electrode or a noble-metal electrode modified by a metal oxide is formed as a nitrogen-oxide converting electrode 2 on a flat, ion conducting, solid electrolyte substrate 1 of zirconia, and a platinum counter electrode 3 is formed on the substrate 1 on the side opposite that having the electrode 2. An oxygen pumping electrode 4 for controlling oxygen concentration is formed on the electrolytic substrate 1 on the same side as that having the converting electrode 2. The counter electrode is formed on the opposite side or shared use is made of the counter electrode of the converting electrode.

Further, a noble-metal electrode, a noble-metal electrode modified by a secondary metal, a noble-metal alloy electrode, a metal-compound electrode or a noble-metal electrode modified by a metal oxide is formed as a nitrogen-oxide sensing electrode 6 on another flat, ion conducting, solid electrolytic substrate 5 of zirconia, and a noble-metal reference electrode 7 that is inactive to nitrogen oxide and active to oxygen is formed on the substrate 5 on the side opposite that having the electrode 6.

Further, a noble-metal oxygen sensing electrode 8 that is inactive to nitrogen oxide and active to oxygen is formed on the substrate 5 on the same side as that having the NOx sensing electrode 6. A spacer 9 consisting of the same solid electrolyte as that of the ion conducting solid electrolytic substrates 1, 5, or of an insulating ceramic material, is interposed between the two substrates 1, 5, which are then bonded together and sintered to form an integrated body. A gas inlet 10 provided in the spacer 9 so as to allow adjustment of nitrogen oxide or oxygen concentration in a measurement chamber 15 must be reduced in diameter to provide diffusion resistance. Though a voltage is applied to the nitrogen-oxide converting electrode 2 to oxidize nitrogen oxide to the peroxide state, the oxidation reaction is dependent upon the electrode material and occurs only within a specific range of potentials. It is necessary, therefore, to apply an optimum voltage to the converting electrode 2. The applied potential of the nitrogen-oxide converting electrode 2 is held at the oxidizing potential of the nitrogen oxide and the concentration of oxygen is regulated to a prescribed value by the oxygen pump so as to oxidize the nitrogen oxide. The electrode reactions at this time can be expressed by the following formulae:

$$2NO_2 + O^{2-} \rightarrow N_2O_5 + 2e^- \quad (1)$$

$$NO_2 + O^{2-} \rightarrow NO_3 + 2e^- \quad (2)$$

$$N_2O_2 + O^{2-} \rightarrow 2NO_3 + 2e^- \quad (3)$$

The electrode equilibrium potential of the product obtained by these reactions tends to be high in comparison with the equilibrium of NO and $NO_2$. This potential is sensed, the rely raising the sensitivity of the sensor.

If the conversion potential is less than 0.1 V, NOx will not be converted. If 1.5 V is exceeded, electrons flow through the solid electrolyte, resulting in inaccuracy. The preferred range, therefore, is 0.4 to 1.0 V.

According to the present invention, it is possible to sense total NOx by oxidizing NOx to as high an oxidized state as possible by electrochemical oxidation irrespective of changes in voltage in different directions owing to NO and $NO_2$ in a conventional mixed potential nitrogen oxide sensor or emf nitrogen sensor. Further, when nitrogen oxide in the highly oxidized stat e is sensed, the standard equilibrium potential of the electrode reaction rises. When the electrode potential at least at this time is compared with the mixed potential or emf that prevails when NOx in the measured gas is oxidized to $NO_2$, it is found that a higher mixed potential value or emf value can be obtained. It has been verified that sensor response time can be shortened by raising the concentration of oxygen in the measurement chamber.

EXAMPLE 1

Figure 2:
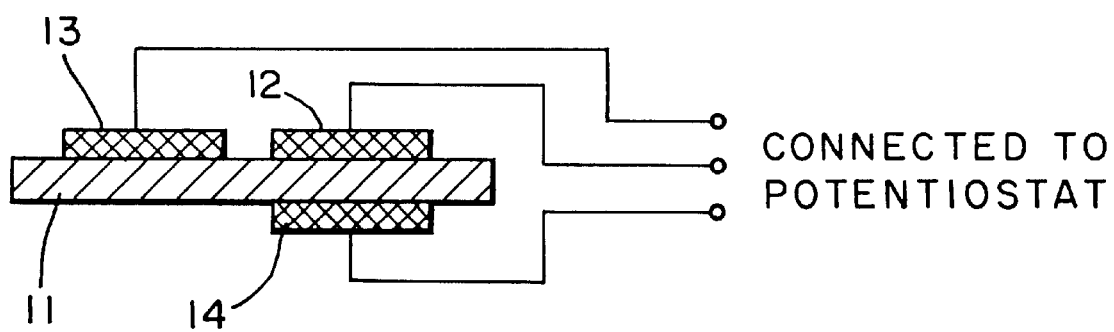
FIG. 2 is a sectional view illustrating a sensor according to another embodiment of the present invention.
Figure 3:
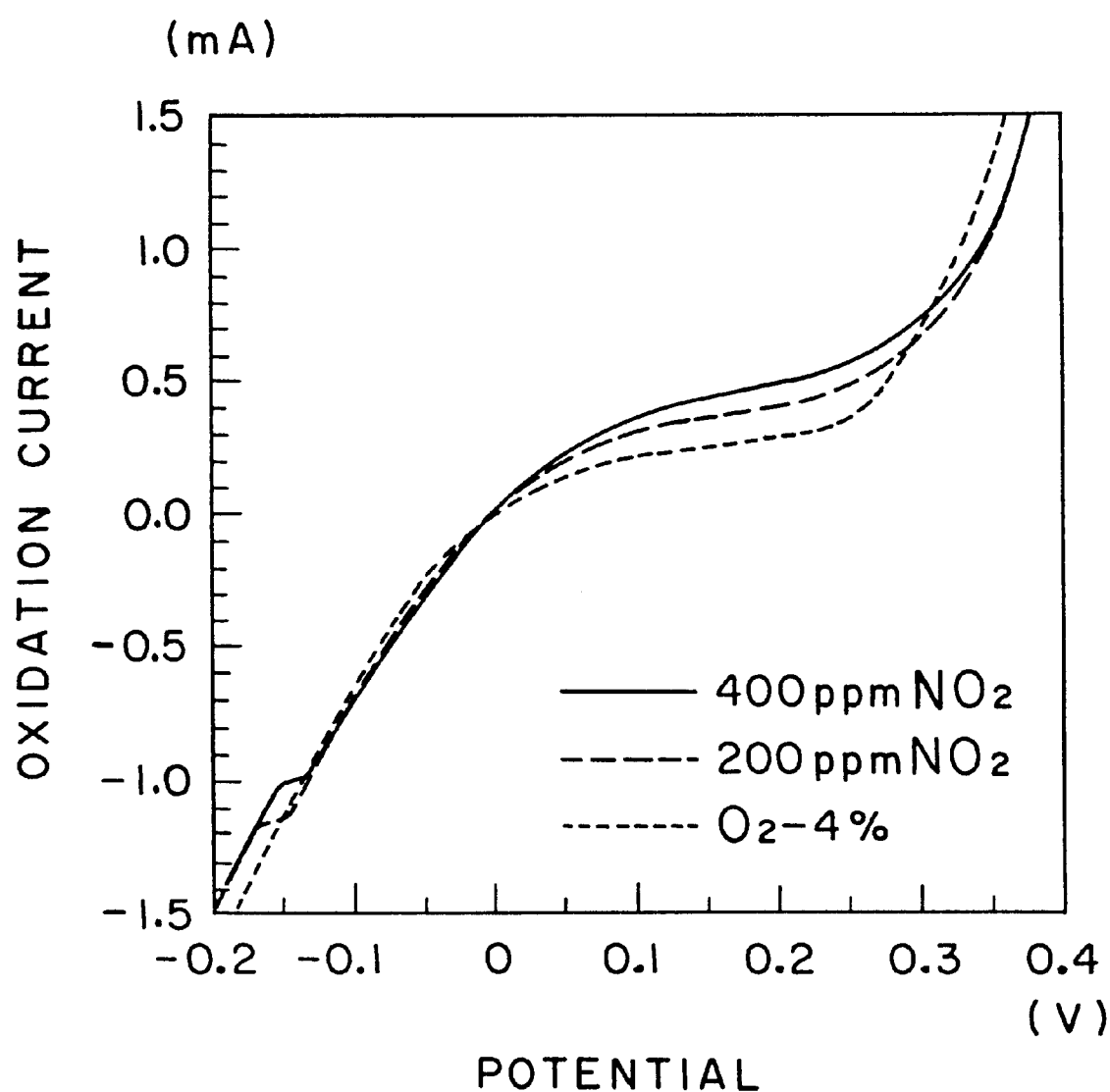
FIG. 3 is a graph showing the relationship between electric potential and oxidization current.

An example of a reaction in which NOx is oxidized by an electrode is illustrated in FIGS. 2 and 3. Three platinum electrodes serving as a specimen electrode 12, reference electrode 13 and counter electrode 14 were formed on a flat, ion conducting, solid electrolytic substrate 11, as shown in FIG. 2. The resulting element was heated to 600° C. and a polarization curve was measured using a potentiostat in a gas obtained by adding 200 ppm of $NO_2$ or 400 ppm of $NO_2$ to oxygen having a nitrogen balance of 4%. The results are as shown in FIG. 3. An $NO_2$ oxidation current was clearly observed in a potential range of 0.05–0.3 V, and it was confirmed that the current is dependent upon the concentration of $NO_2$. This clearly evident oxidation current was not observed when the NO at the same concentration was introduced in similar fashion. Accordingly, it is construed that the oxidation current shown in FIG. 3 is a current produced by $N_2O_5$ or $NO_3$, depending upon the oxidation of $NO_2$. The electrode re actions are expressed by the reaction formulae (1), (2) and (3) cited above.

It should be noted that a measurement was taken using a platinum electrode modified by the oxide $NiCr_2O_4$. Though the results indicated that the oxidation potential region of $NO_2$ shifted toward the high potential side, namely to the region of 0.3–0.6 V, a similar oxidation current based upon $NO_2$ was measured.

The foregoing results confirm that $NO_2$ is oxidized to nitrogen oxide of a higher state of oxidation owing to the electrode reactions.

EXAMPLE 2

Figure 4:
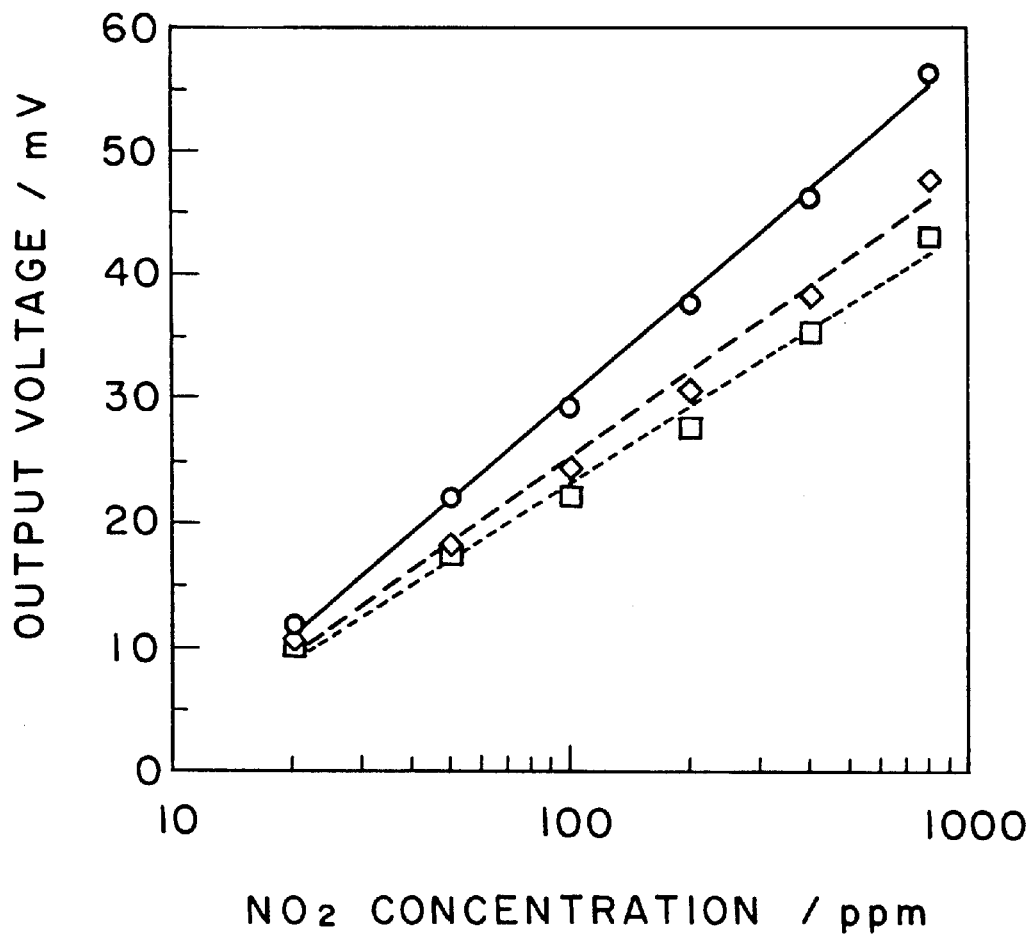
FIG. 4 is a graph $NO_2$ concentration and detection voltage.

A converting section for oxidizing nitrogen oxide and comprising a platinum electrode modified by the oxide $NiCr_2O_4$ and a platinum counter electrode was fabricated. The modified platinum electrode was formed on a flat, ion conducting, solid electrolytic substrate of zirconia and the counter electrode was formed on same substrate but on the opposite side. An $NiCr_2O_4$ sensing electrode was formed on another flat, ion conducting, solid electrolytic substrate of zirconia and a reference electrode was formed on the same substrate but on the opposite side, thereby forming a measurement chamber in a manner similar to that shown in FIG. 1. The resulting sensor element was heated to 600° C., the voltage of the converting electrode of the nitrogen oxide converting section was held at a prescribed value in a 4% oxygen environment having a balance of nitrogen, the concentration of introduced $NO_2$ was changed and a change in the potential of the NOx sensing electrode was measured across the reference electrode. The voltage of the NOx converting section was then varied and the change in the potential of the NOx sensing electrode was measured. The results obtained are illustrated in FIG. 4. When the sensitivity of the sensor and the slope of the sensitivity obtained when the voltage applied to the NOx converting section was held at 0.8 V is compared with the sensitivity and slope of the sensitivity when the applied voltage was held at 0.4 V or 1.0 V, it is seen that the former are larger due to the value of potential in the conversion electrode. More specifically, if the polarization potentials of both the converting electrode and its counter electrode are taken into consideration, the major part of 0.8 V are apportioned to the two electrodes and the potential of the converting electrode resides in the oxidation potential region of the nitrogen oxide. The introduced $NO_2$, therefore, is oxidized further and the sensitivity of the sensor rises.

Figure 5:
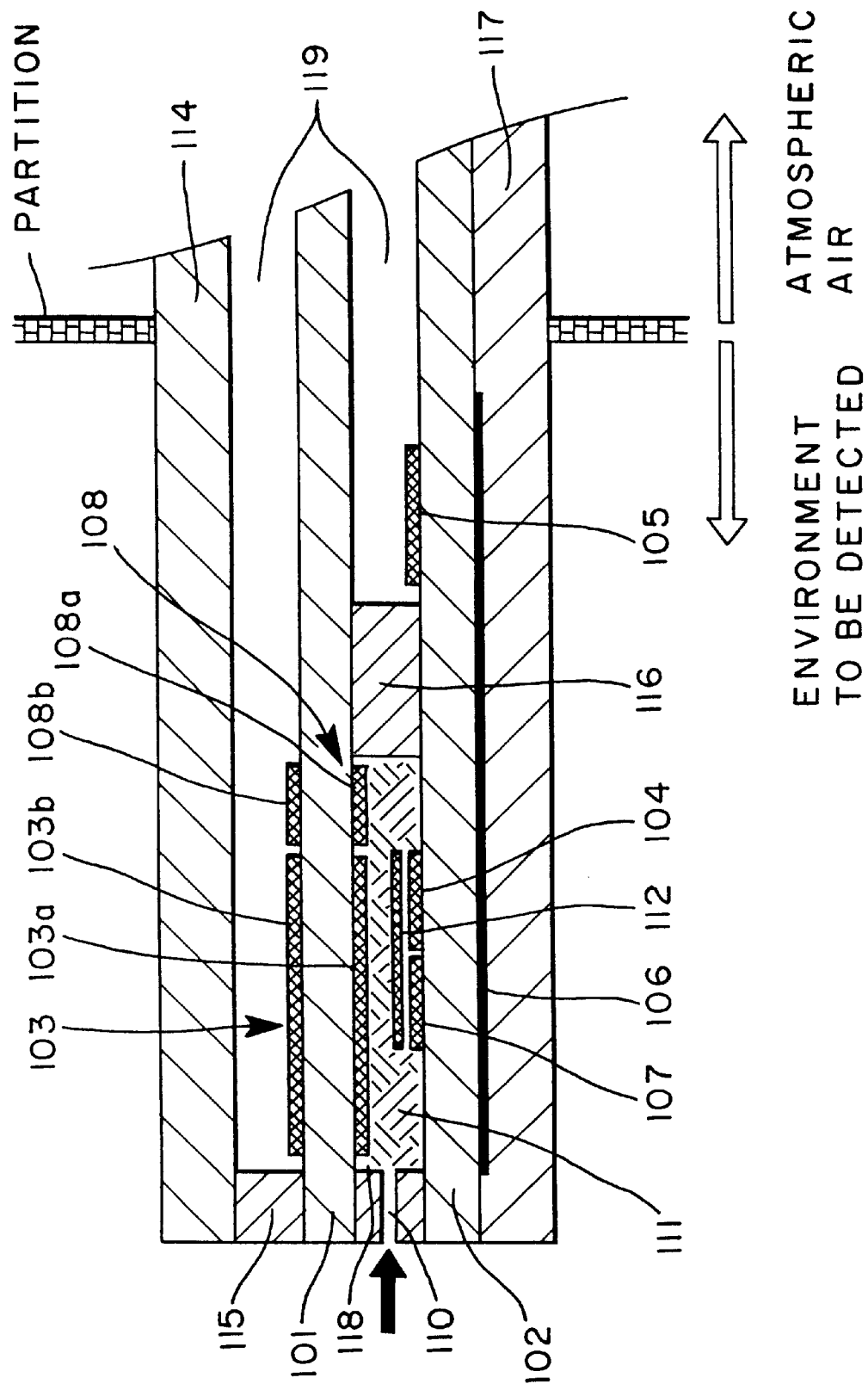
FIG. 5 is a sectional view illustrating a nitrogen oxide sensor constructed from a single chamber according to the present invention.
Figure 6:
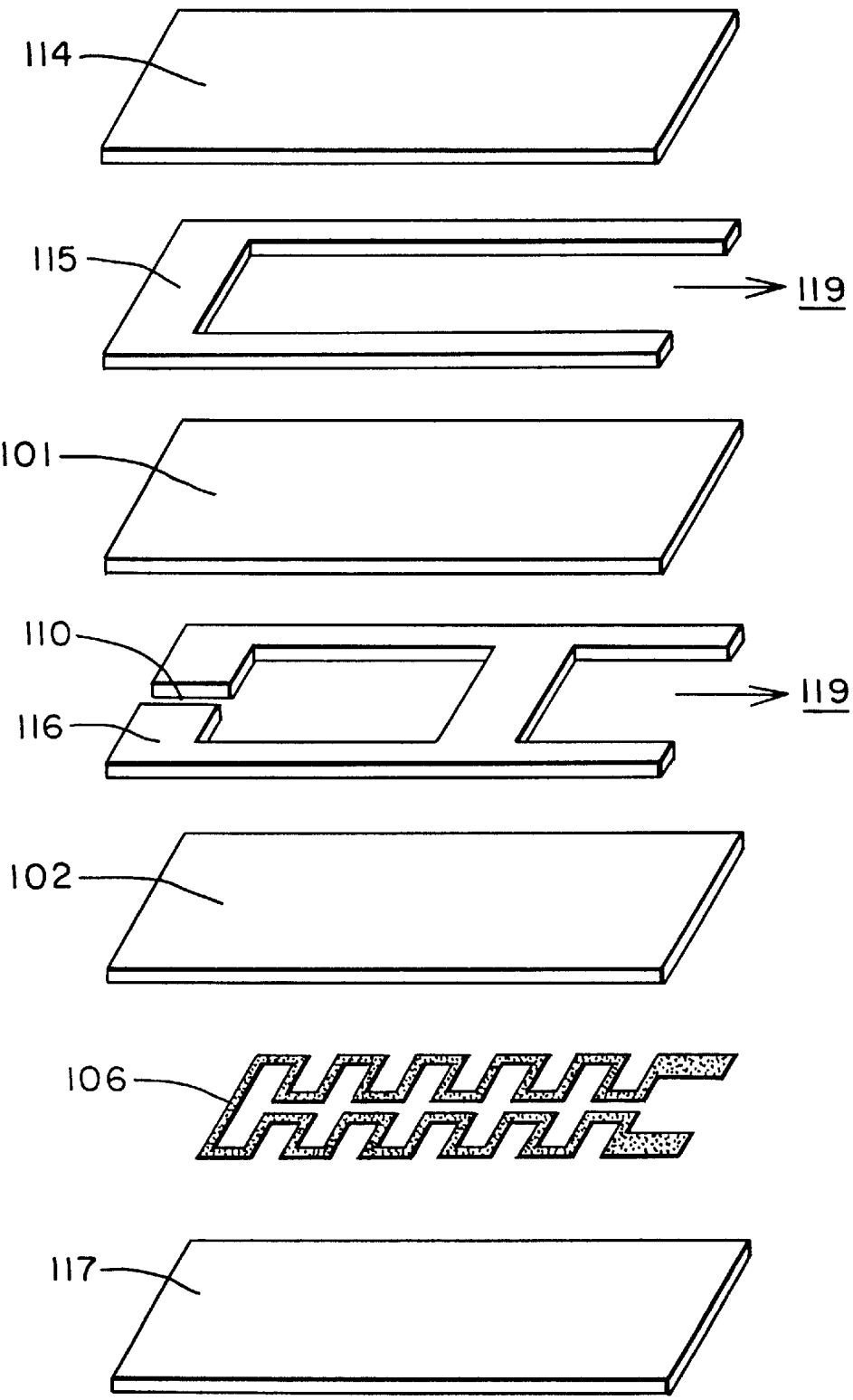
FIG. 6 is an exploded perspective view illustrating a nitrogen oxide sensor constructed from a single chamber according to the present invention.

FIGS. 5 and 6 are diagrams illustrating a nitrogen oxide sensor constructed from a single chamber according to the present invention. The present invention will now be described taking this arrangement as an example.

Plate-shaped solid electrolytes 101, 102 comprise various electrolytes the foremost of which are stabilized zirconia and partially stabilized zirconia. Any electrolytic material can be used, so long as it exhibits oxygen ion conductivity, irrespective of stabilizers and the amount thereof added.

An oxygen pump 103 includes the plate-shaped solid electrolyte 101 and a pair of electrodes 103a, 103b disposed on both sides of the electrolyte 101. The oxygen pump 103 acts as an oxygen pumping cell when a prescribed voltage is applied across the electrodes 103a, 103b. As long as the electrodes 103a, 103b consist of a material that undergoes electrochemical pumping, there is no particular limitation upon the material and well-known materials can be used. These electrodes are obtained by forming a paste of the electrode material using a well-known film forming method such as screen printing and then sintering the paste at a prescribed temperature. It is preferred that the electrodes be extremely fine-grained electrodes, desirably formed by sputtering, having many activity points that contribute to pumping.

The NOx sensing cell consists of the solid electrolyte 102, a sensing electrode 104 and an counter electrode 105. At least the sensing electrode 104 is formed in a chamber 118 in which the electrode 103a of the oxygen pump 103 is formed. The counter electrode 105 may or may not be placed in the chamber 118 in the same manner as the sensing electrode 104. However, if the counter electrode 105 exhibits some activity to NOx gas, it will have an influence upon a signal based upon the concentration of NOx sensed by the sensing electrode 104. In such case, therefore, it is preferred that the counter electrode 105 be provided in a duct 119 communicating with the atmospheric air, which is the reference environment. Further, the sensing electrode 104 and/or counter electrode 105 may be formed on the solid electrolyte 101 constructing the oxygen pumping cell.

As long as the sensing electrode 104 is an electrode material exhibiting activity with respect to NOx gases, there is no particular limitation upon the material and well-known materials can be used. This electrode is obtained by forming a paste of the electrode material using a well-known film forming method such as screen printing and then sintering the paste at a prescribed temperature. It is preferred that the electrode be an extremely fine-grained electrode, desirably formed by sputtering, having many activity points that contribute to sensitivity to NOx gases. If the concentration of oxygen in the NOx gas sensing cell or in the chamber is 0.01–10%, NOx gas concentration can be sensed accurately. An oxygen concentration of less than 0.1% results in a lower speed of response. An oxygen concentration of greater than 5% results in a lower speed of response with some decline in sensitivity to NOx. A range of oxygen concentrations of 0.1–5% is preferred for a sensor mounted in an area where a high speed of response is required.

In the case of an automotive vehicle, the concentration of oxygen present in the environment of the exhaust gas falls within a wide range depending upon the state of combustion, i.e., the air-fuel ratio. In addition, when oxygen in excess of the equivalent of oxygen necessary to sufficiently oxidize NO gas, hydrocarbon gases and CO gas is pumped in, it is desirable to operate an auxiliary oxygen pump 108 to make the oxygen concentration 0.01–10% not only in the NOx gas sensing cell but also in the entirety of the chamber 118.

The auxiliary oxygen pump 108 may be constituted either by the solid electrolyte 101 or by the solid electrolyte 102 on which the NOx sensing electrode 104 has been formed. The auxiliary oxygen pump 108 includes at least either the solid electrolyte 101 or 102, which is formed in the shape of a plate, an electrode 108a fixed to this solid electrolyte and disposed in the chamber 118, and an electrode 108b placed outside of the chamber 118. Applying a prescribed voltage across the two electrodes 108a, 108b causes these components to operate as an auxiliary oxygen pump. That is, if the concentration of oxygen in the chamber 118 is lower than the prescribed range of oxygen concentrations, an oxygen pumping operation is performed so as to pump in oxygen from external electrode 108b disposed so as to communicate with the atmospheric air.

Conversely, if the concentration of oxygen in the chamber 118 is greater than the prescribed range of oxygen concentrations, an oxygen pumping operation is performed so as to discharge oxygen from the electrode 108a within the chamber 118. As long as the electrodes 108a, 108b consist of a material that undergoes electrochemical pumping in a manner similar to the electrodes 103a, 103b, there is no particular limitation upon the material. These electrodes are obtained by forming a paste of the electrode material using a well-known film forming method such as screen printing and then sintering the paste at a prescribed temperature. It is preferred that the electrodes be extremely fine-grained electrodes, desirably formed by sputtering, having many activity points that contribute to pumping.

The sensing of NOx gases can be performed more accurately by constructing an oxygen sensor for the purpose of controlling the oxygen concentration in the NOx gas sensing cell or in the chamber 118. An electrode 107 for sensing oxygen concentration is formed on the solid electrolyte 101 or 102 in the chamber 118 in an area near the NOx gas sensing cell and, by making shared use of the counter electrode 105, oxygen concentration is measured based upon the potential difference developed between these two electrodes. It is preferred that the counter electrode 105 be provided in the duct 119 communicating with the atmospheric air, which is the reference environment.

By controlling the driving voltage of the oxygen pump 103 and/or auxiliary oxygen pump 108 based upon the oxygen concentration measured by the oxygen sensor cell, the oxygen concentration in the chamber 118 can be controlled and the concentration of NOx gases can be sensed in highly accurate fashion. The electrode 107 for sensing oxygen concentration is obtained by forming a paste of the electrode material using a well-known film forming method such as screen printing and then sintering the paste at a prescribed temperature.

In this arrangement of the present invention, the operation through which nitrogen oxide gas is oxidized to $NO_2$ gas, a gas of a peroxide of nitrogen of order greater than $NO_2$ or to mixture of these gases and the operation for measuring the potential difference that develops at the NOx sensing cell via the solid electrolyte must be made to occur in reliable fashion. To accomplish this, the operating temperature is an important factor and it is necessary to control the oxygen pumping cell and the NOx gas sensing cell by a heating mechanism so as to fall within a temperature range of 400–750° C. In other words, at a temperature below 400° C., the ion conductivity of the solid electrolyte per declines and it becomes difficult to obtain a stabilized output. At temperatures above 750° C., on the other hand, oxidizing NO gas is difficult and measurement intended by this application cannot be carried out. Accordingly, it is required that at least the NOx gas sensing cell be maintained in the above-mentioned temperature range and, more preferably, in a temperature range of 500–700° C.

As an example of the heating mechanism, use is made of a plate-shaped heater 106 having embedded platinum heating elements that are highly stable. The plate-shaped heater 106 is affixed to the solid electrolyte 102, in which the oxygen pumping cell or NOx sensing cell has been formed, or to partitions 115 and 114 having the ducts 119 communicating with the atmosphere. The heater 106 may of course be disposed on both sides so as control the temperatures of the oxygen pumping cell and NOx sensing cell individually. Methods of controlling temperature include feedback control based upon the electrical resistance of the heater itself and feedback control by a temperature sensor such as a separately provided thermocouple.

The gas in the measurement environment is introduced into the chamber 118 from a gas inlet port 110. With the oxygen concentration in the chamber 118 or, more correctly, the oxygen concentration in the NOx sensing cell, at 0.01 to 10%, it is necessary to control the voltage applied to the oxygen pump 103 in such a manner that NO gas in nitrogen oxide gases will be oxidized to at least $NO_2$ gas. When the long-term stability of the electrodes 103a, 103b constructing the oxygen pump 103 and of the solid electrolyte on which both electrodes have been formed is taken into consideration, it is preferred that the applied voltage be less than 1.5 V. The gas inlet 110 is required to have a gas diffusion resistance that will make it possible to convert the nitrogen oxide gases and to control the oxygen concentration of the NOx gas sensing cell to 0.01–10%. In the case where the auxiliary oxygen pump 108 has been constructed to make the oxygen concentration in chamber 118 equal to 0.01–10%, the gas inlet 110 will have a gas diffusion resistance that will make possible this control of the oxygen concentration at an applied voltage of less than 1.5 V in regard to the voltage applied to the auxiliary oxygen pump 108.

A catalyst 111 for oxidizing nitrogen oxide gases is formed in the chamber 118. This is to prevent NOx gas, which has been converted in the oxygen pump 103, from being reduced again to NO gas. It is preferred that the oxidizing catalyst 111 be provided to fill the chamber 118.

In a case where the electrode 103a of the oxygen pump 103 and at least the sensing electrode 104 that forms the NOx gas sensing cell oppose each other, a porous body 112 is placed between the electrode 103a and at least the sensing electrode 104 and the gap between these electrodes is reduced, thereby making it possible to immediately sense, by the NOx gas sensing electrode, the NOx gas that has been converted by the oxygen pump 103. A better effect is obtained if the porous body 112 makes shared use of the oxidizing catalyst 111. If the porous body 112 is a material having a high electrical insulation, the signal output of the NOx gas sensing cell can be extracted without being influenced by the voltage that drives the oxygen pump 103. If the circuit constructing the oxygen pump and the circuit constructing the NOx gas sensing cell are entirely separate, the porous body 112 can be used without problem even if it is electrically conductive.

Figure 7:
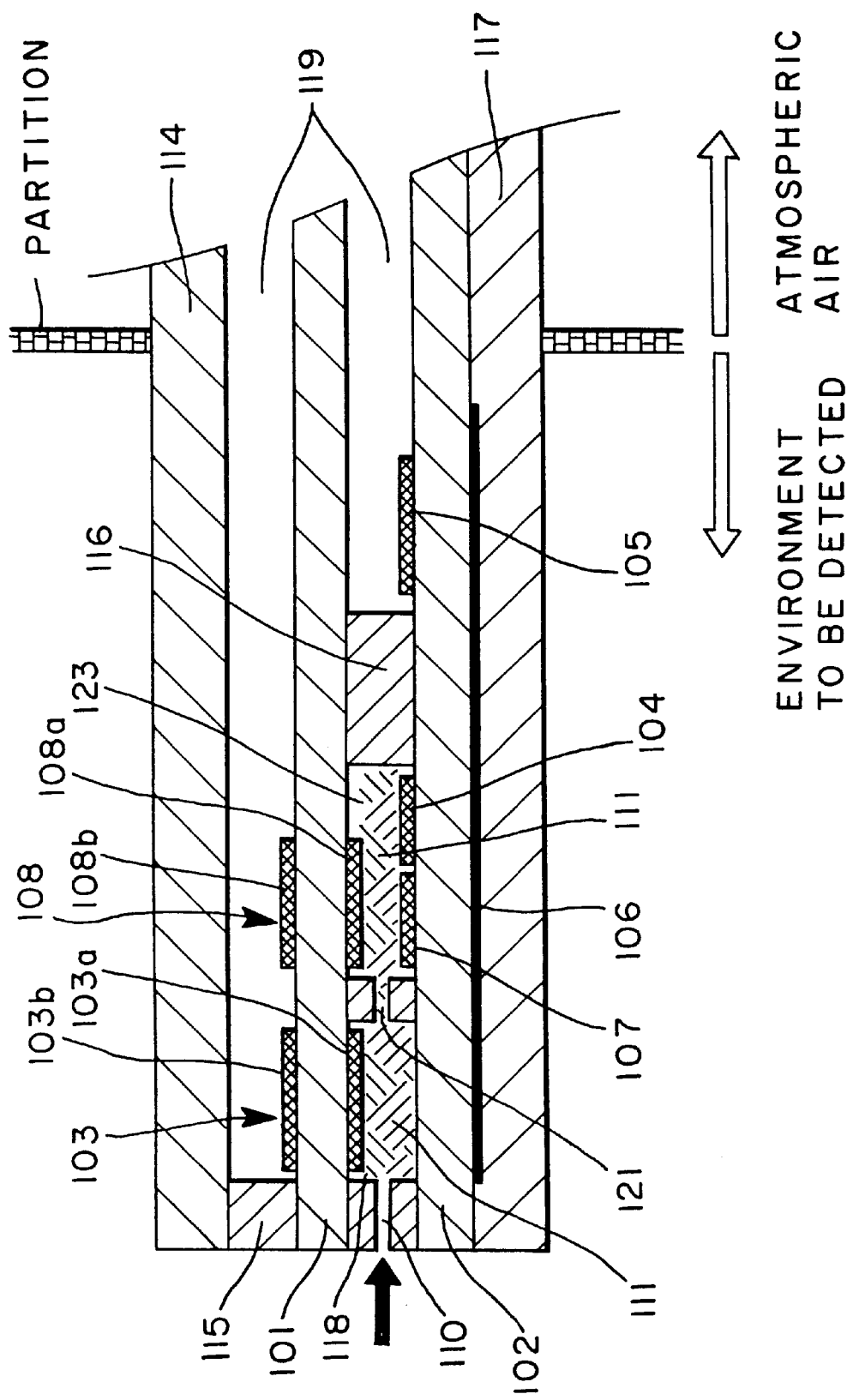
FIG. 7 is a sectional view illustrating a nitrogen oxide sensor constructed from two chambers according to the present invention.
Figure 8:
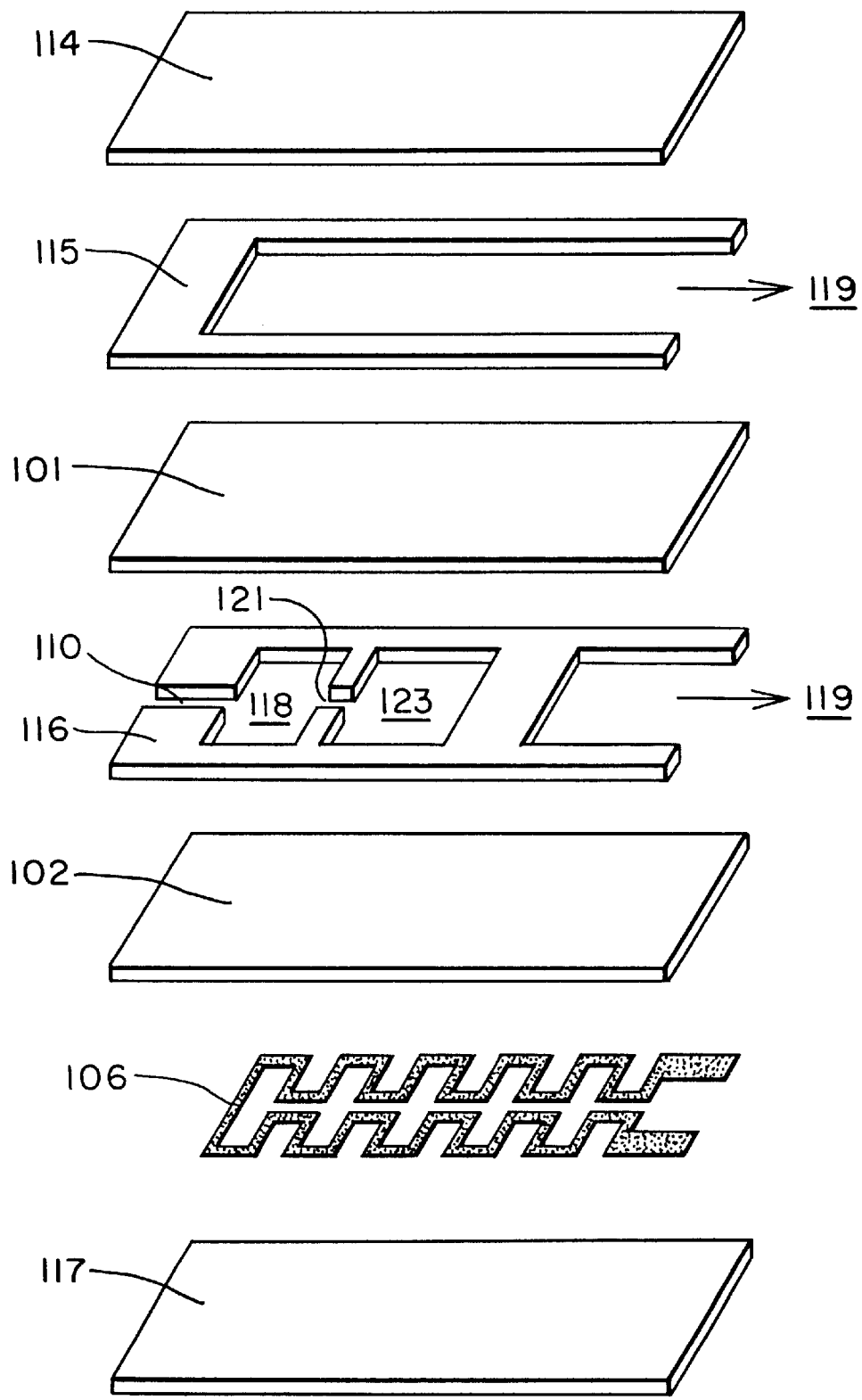
FIG. 8 is an exploded perspective view illustrating a nitrogen oxide sensor constructed from two chambers according to the present invention.

FIGS. 7 and 8 are diagrams illustrating a nitrogen oxide sensor constructed from two chambers according to the present invention. The present invention will now be described taking this arrangement as an example. It should be noted that the basic arrangement inclusive of the constituent materials and method of formation is in accordance with the detailed description rendered in accordance with FIGS. 5 and 6.

The solid electrolyte 101 constructing the oxygen pump 103 is plated-shaped and has the electrodes 103a, 103b on both its sides. The oxygen pump 103 acts as an oxygen pumping cell when a prescribed voltage is applied across the electrodes 103a, 103b. The electrode 103a constructing the oxygen pump 103 is formed in the chamber 118, which is defined by a partition 116. Amongst the nitrogen oxide gases in the environment undergoing detection, NO gas in particular is oxidized and converted to $NO_2$ gas, gas of a peroxide of nitrogen of order greater than $NO_2$ or to mixture of these gases In addition, oxygen in excess of the equivalent of oxygen necessary to oxidize reducing gases, such as hydrocarbon gases and CO gas that coexist with NOx gas, must be pumped into the chamber 118.

The NOx gas sensing cell comprises the solid electrolyte 102, the sensing electrode 104 and the opposing electrode 105. At least the sensing electrode 104 is formed in a second chamber 123 defined by the partition 116. The counter electrode 105 may or may not be placed in second chamber 123 in the same manner as the sensing electrode 104. However, it is preferred that the counter electrode 105 be provided in the duct 119 communicating with the atmosphere, which is the reference environment. Further, the sensing electrode 104 and/or counter electrode 105 may be formed on the solid electrolyte 101 constructing the oxygen pumping cell.

If the concentration of oxygen in the NOx gas sensing cell or in the chambers is 0.01–10%, NOx gas concentration can be sensed accurately. However, the preferred range of oxygen concentrations is 0.1–5%, as mentioned earlier.

Accordingly, it is desirable to operate the auxiliary oxygen pump 108 that is for controlling the oxygen concentration in the second chamber 123. The auxiliary oxygen pump 108 may be constituted either by the solid electrolyte 101 or by the solid electrolyte 102 on which the NOx sensing electrode 104 has been formed. The auxiliary oxygen pump 108 includes at least either the solid electrolyte 101 or 102, which is formed in the shape of a plate, the electrode 108a disposed in the second chamber 123, and the electrode 108b placed outside of the chamber. Applying a prescribed voltage across the two electrodes 108a, 108b causes these components to operate as an auxiliary oxygen pump. That is, if the concentration of oxygen in the second chamber 123 is lower than the prescribed range of oxygen concentrations, an oxygen pumping operation is performed so as to pump in oxygen from external electrode 108b disposed so as to communicate with the atmosphere.

Conversely, if the concentration of oxygen in the second chamber 123 is greater than the prescribed range of oxygen concentrations, an oxygen pumping operation is performed so as to discharge oxygen from the electrode 108a within the second chamber 123. The oxygen concentration in the second chamber 123 is measured by the oxygen sensing cell. The electrode 107 for sensing oxygen concentration is formed on the solid electrolyte 101 or 102 in the second chamber 123 in an area near the NOx gas sensing cell and, by making shared use of the counter electrode 105 of the NOx gas sensing cell, oxygen concentration is measured based upon the potential difference developed between these two electrodes. It is preferred that the counter electrode 105 be provided in the duct 119 communicating with the atmospheric air, which is the reference environment.

By controlling the driving voltage of the auxiliary oxygen pump 108 based upon the oxygen concentration measured by the oxygen sensing cell, the oxygen concentration in the second chamber 123 can be controlled and the concentration of NOx gases can be sensed in highly accurate fashion.

The nitrogen oxide gas is oxidized to at least $NO_2$ by the oxygen pump 103 formed in the first chamber 118, and the reducing gas that coexists in the gas of the measurement environment also is oxidized so that any interference with NOx gases can be eliminated. Furthermore, by forming an oxidation catalyst in the first chamber 118 and second chamber 123 or filling these chambers with this catalyst, converted NOx gases reach the NOx gas sensing cell without being reduced again, thus making the highly accurate sensing of NOx concentration possible. The heating mechanism in this arrangement of the present invention is in accordance with the description rendered in connection with FIG. 5.

The gas in the measurement environment is introduced into the first chamber 118 from the gas inlet port 110 and into the second chamber 123 from the first chamber 118 through a passageway 121 leading to the second chamber 123. The voltage applied to the oxygen pump 103 is controlled in such a manner that nitrogen oxide gases are oxidized to at least $NO_2$. When the long-term stability of the electrodes 103a, 103b constructing the oxygen pump 103 and of the solid electrolyte on which both electrodes have been formed is taken into consideration, it is preferred that the applied voltage be less than 1.5 V. Accordingly, at least one of the gas inlet 110 and passageway 121 has gas diffusion resistance. In the case where the auxiliary oxygen pump 108 has been constructed to make the oxygen concentration in the second chamber 123 equal to 0.01–10% or higher, the passageway 121 from the first chamber to the second chamber will have a gas diffusion resistance that will make possible this control of the oxygen concentration at an applied voltage of less than 1.5 V in regard to the voltage applied to the auxiliary oxygen pump 108.

In any of the arrangements described in connection with FIGS. 5 through 8, the output signal in the NOx gas sensing cell is corrected using the output signal in the oxygen sensing cell disposed in the chamber and is detected as the emf value of the NOx gas, thereby making it possible to reduce the influence of the concentration of coexisting oxygen. The result is more accurate sensing of nitrogen oxide gases. Further, in a case where a mixed potential is produced by the NOx sensing electrode 104 owing to concurrent electrochemical reactions with oxygen and NOx, forming the sensing electrode 104 and the opposing electrode 105 in the same chamber reduces susceptibility to the influence of coexisting oxygen concentration and improves the accuracy of nitrogen oxide gas detection. In addition, it is unnecessary to separately form an atmospheric duct for the counter electrode.

It is possible to construct a nitrogen oxide sensor which uses an oxygen pump to pump in or discharge oxygen electrochemically, whereby the concentration of oxygen in the NOx gas sensing cell is controlled to fall within a range of 0.01 to 10%, thereby oxidizing NO gas and eliminating interference with nitrogen oxide gases as well as interference with coexisting reducing gas, thereby providing high sensitivity and stability.

This aspect of the present invention will now be described in detail with reference to specific examples, though the invention is in no way limited to these examples.

EXAMPLE 3

A nitrogen oxide sensor comprising the oxygen pump 103, the auxiliary oxygen pump 108, the NOx gas sensing cell 104 and the oxygen sensing cell 107 from among the components shown in FIG. 5 was fabricated using the materials and procedure set forth below. To fabricate the oxygen pump 103, use was made of a green sheet comprising a 6 mol % yttrium-stabilized zirconia substrate having dimensions of 0.2 (thickness)×6 (width)×180 mm. Electrodes were formed in both the chamber and atmospheric duct by applying platinum paste to the green sheet by screen printing.

As for the NOx gas sensing cell 104, use was made of a green sheet of the same material and dimensions as those of the oxygen pump. A sensing electrode was formed in the chamber by applying a compound oxide paste of $NiCr_2O_4$ to the green sheet by screen printing. Further, a sensing electrode was formed in the atmospheric duct by applying platinum paste to the green sheet by screen printing. The compound oxide paste of $NiCr_2O_4$ was obtained by using a ball mill to grind $NiCr_2O_4$ powder, manufactured by a solid-phase method, drying the ground powder and then compounding it with ethyl cellulose and a diligent.

The auxiliary oxygen pump 108 was fabricated downstream of the oxygen pump 103 on the green sheet constituting the oxygen pump 103. Electrodes were formed in both the chamber and atmospheric duct by applying platinum paste to the green sheet by screen printing.

The oxygen sensing cell 107 was fabricated on the green sheet constituting the NOx gas sensing cell. The electrode for sensing oxygen concentration within the chamber was formed by applying platinum paste to the green sheet by screen printing. The counter electrode was obtained by sharing the counter electrode of the NOx gas sensing cell.

The heater 106 was formed by the screen printing of a high-purity platinum paste different from that for the electrodes. A high-purity alumina printed layer was formed on a green sheet of the same material and dimensions as those of the oxygen pump, a heating pattern was printed on the printed layer and a further high-purity alumina layer was formed on the heater pattern.

The size of the gas inlet was made 0.1 (thickness)×0.5 (width)×11 mm. The thickness of the chamber wall green sheet constructing the chamber was made 40 µm.

The green sheets having the electrodes and heater formed on them in the manner described above were stacked into a laminate and sintered at 1400° C. for 5 hrs, thereby fabricating a nitrogen oxide sensor having an integrated oxygen pumping cell, NOx gas sensing cell and heater.

The fabricated sensor was placed in a simulation gas of known composition while held at a temperature of 600° C. by the embedded heater. The output of the sensor was examined under these conditions. The auxiliary oxygen pump was controlled so as to make the oxygen concentration in the chamber equal to 4%, and a voltage was applied to the oxygen pumping cell so as to draw oxygen into the chamber.

The results are as shown in Table 1. An output proportional to the logarithm of the sum of the $NO_2$ and NO gas concentrations was obtained without influence from the concentrations of $C_3H_6$, CO and oxygen.

TABLE 1

| | SIMULATION GAS COMPOSITION | | | | | | SENSOR |
|---|---|---|---|---|---|---|---|
| NO. | NO (ppm) | $NO_2$ (ppm) | $O_2$ (%) | $C_3H_6$ (ppm) | CO (ppm) | $N_2$ (ppm) | NO + $NO_2$ (ppm) | OUTPUT (mV) |
| 1 | 50 | 0 | 0.005 | 0 | 0 | bal. | 50 | 35 |
| 2 | 50 | 50 | 0.005 | 0 | 0 | bal. | 100 | 50 |
| 3 | 100 | 50 | 0.005 | 0 | 0 | bal. | 150 | 60 |
| 4 | 100 | 50 | 0.005 | 100 | 0 | bal. | 150 | 60 |
| 5 | 100 | 50 | 0.005 | 100 | 100 | bal. | 150 | 61 |
| 6 | 100 | 50 | 0.5 | 100 | 100 | bal. | 150 | 61 |
| 7 | 100 | 50 | 10 | 100 | 100 | bal. | 150 | 59 |

EXAMPLE 4

A nitrogen oxide sensor comprising the oxygen pump, the auxiliary oxygen pump, the NOx gas sensing cell and the oxygen sensing cell from among the components shown in FIG. 7 was fabricated. The materials and qualities of these components, their dimensions and the sintering conditions were the same as in Example 3.

The oxygen pump was constructed in the first chamber and the NOx gas sensing cell, the auxiliary oxygen pump and the oxygen sensing cell were constructed in the second chamber. The counter electrode was formed in an atmospheric duct and shared use was made of the counter electrode of the oxygen sensor.

The fabricated sensor was placed in a simulation gas of known composition while held at a temperature of 600° C. by the embedded heater. The output of the sensor was examined. The auxiliary oxygen pump was controlled so as to make the oxygen concentration in the chamber equal to 4%, and a voltage was applied to the oxygen pumping cell so as to draw oxygen into the chamber. The results are as shown in Table 2. An output proportional to the logarithm of the sum of the $NO_2$ and NO gas concentrations was obtained without influence from the concentrations of $C_3H_6$, CO and oxygen.

of oxygen in the second chamber on sensitivity to NOx and on the speed of response were examined. The oxygen concentration in the chamber was measured by the oxygen sensor and controlled by the auxiliary oxygen pump. The materials and qualities of these components, their dimensions and the sintering conditions were the same as in Example 4.

Figure 9:
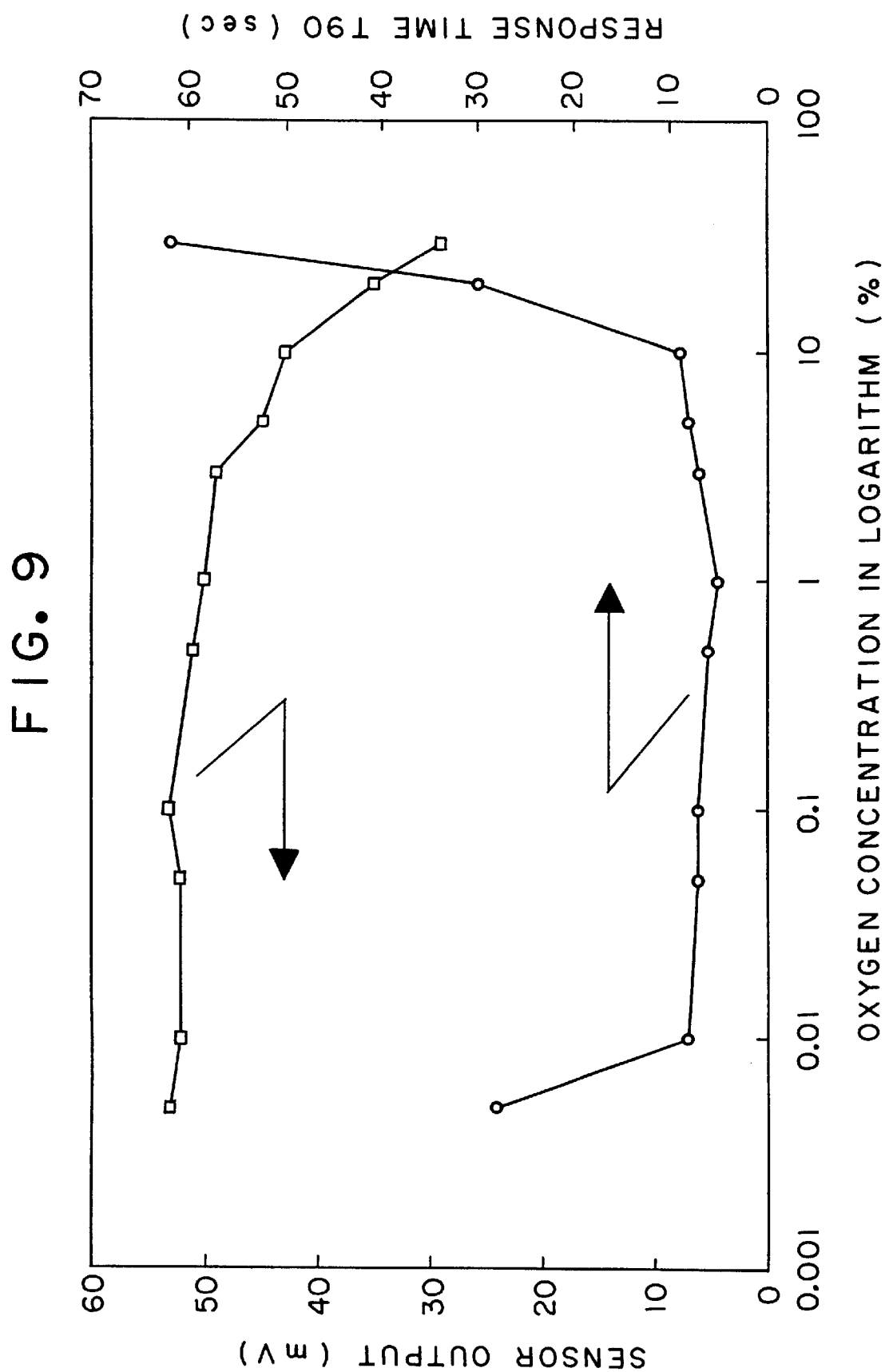
FIG. 9 is a graph illustrating the dependence of sensor output and response speed on oxygen concentration in case of a nitrogen oxide sensor constructed from two chambers according to the present invention.

The fabricated sensor was placed in NOx gases consisting of 500 ppm NO and 50 ppm $NO_2$ while held at a temperature of 600° C. by the embedded heater. The output of the sensor was examined and the results are as shown in FIG. 9. Sensitivity to NOx was high and there was a marked increase in speed of response at oxygen concentrations below 0.01%. Sensitivity to NOx was somewhat lower and there was a marked increase in speed of response at oxygen concentrations above 10%.

EXAMPLE 6

A nitrogen oxide sensor comprising the oxygen pump, the auxiliary oxygen pump, the NOx gas sensing cell, the oxygen sensing cell and the porous body from among the components shown in FIG. 5 was fabricated. The thickness of the chamber wall green sheet constructing the chamber was made 40 μm and the oxygen pump electrode in the chamber and the NOx sensing electrode were made to contact each other via a porous film of alumina. Further, a sensor was fabricated in such a manner that the oxygen pump electrode in the chamber and the NOx sensing electrode were made to contact each other via a porous film

TABLE 2

| | SIMULATION GAS COMPOSITION | | | | | | SENSOR |
|---|---|---|---|---|---|---|---|
| NO. | NO (ppm) | $NO_2$ (ppm) | $O_2$ (%) | $C_3H_6$ (ppm) | CO (ppm) | $N_2$ (ppm) | NO + $NO_2$ (ppm) | OUTPUT (mV) |
| 1 | 50 | 0 | 0.005 | 0 | 0 | bal. | 50 | 36 |
| 2 | 50 | 50 | 0.005 | 0 | 0 | bal. | 100 | 51 |
| 3 | 100 | 50 | 0.005 | 0 | 0 | bal. | 150 | 60 |
| 4 | 100 | 50 | 0.005 | 100 | 0 | bal. | 150 | 61 |
| 5 | 100 | 50 | 0.005 | 100 | 100 | bal. | 150 | 62 |
| 6 | 100 | 50 | 0.5 | 100 | 100 | bal. | 150 | 60 |
| 7 | 100 | 50 | 10 | 100 | 100 | bal. | 150 | 63 |

EXAMPLE 5

A nitrogen oxide sensor comprising the oxygen pump, the auxiliary oxygen pump, the NOx gas sensing cell and the oxygen sensing cell from among the components shown in FIG. 7 was fabricated and the influence of the concentration obtained by supporting palladium on alumina. The materials and qualities of the oxygen pump, auxiliary oxygen pump, NOx gas sensing cell and oxygen sensing cell, their dimensions and the sintering conditions were the same as in Example 1. The counter electrode was formed in an atmospheric duct and shared use was made of the counter electrode of the oxygen sensor.

Figure 10:
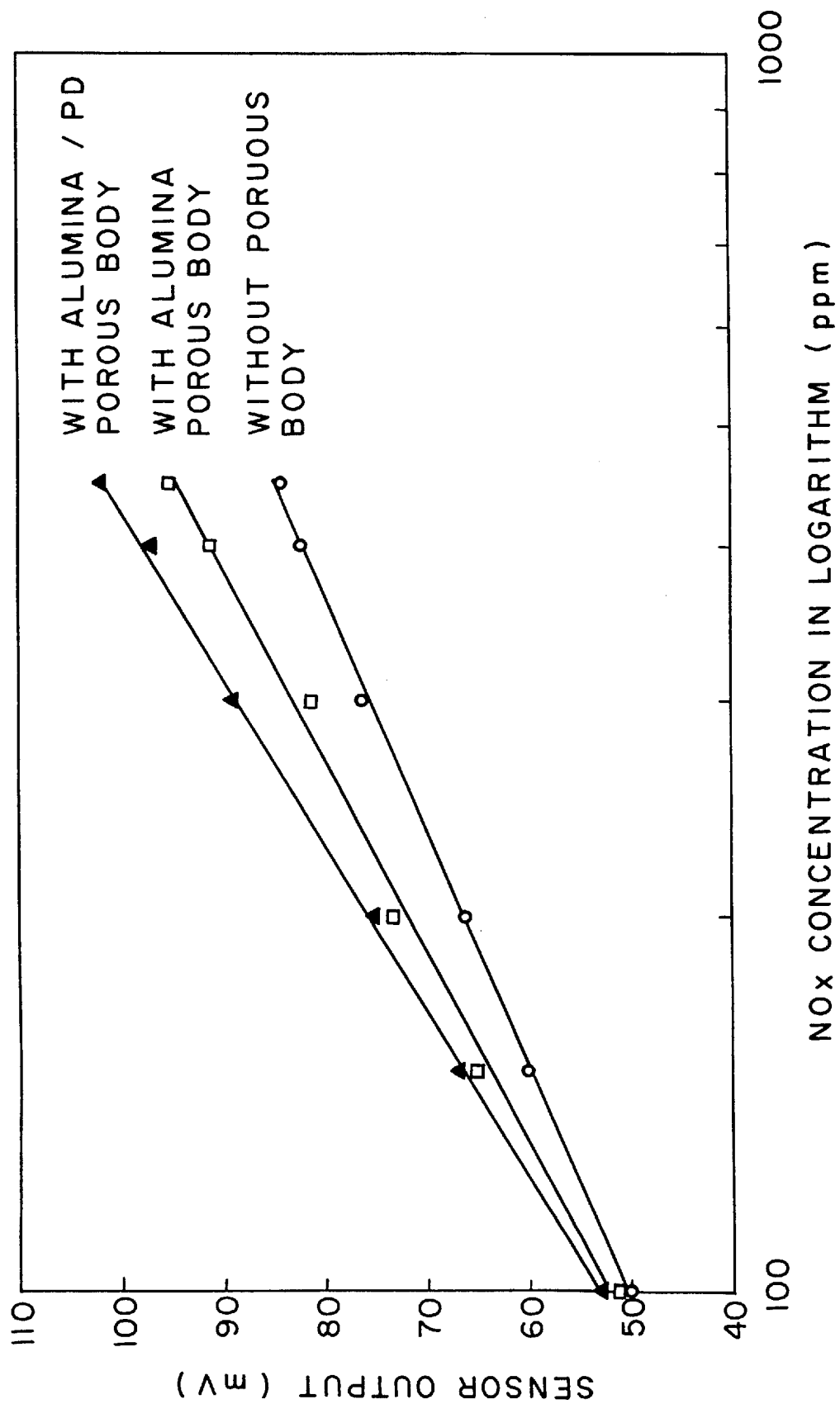
FIG. 10 is a graph illustrating the effect of a porous body on the relationship between NOx concentration and sensor output in case of a nitrogen oxide sensor constructed from one chamber according to the present invention.

The fabricated sensors were placed in NOx gases consisting of 50–400 ppm NO and 50 ppm $NO_2$ while held at a temperature of 600° C. by the embedded heater. The output of the sensor was examined. The auxiliary oxygen pump was controlled so as to make the oxygen concentration in the chamber equal to 4%. The results are as shown in FIG. 10. For the sake of comparison, measurement was also performed using the sensor illustrated in Example 4 and these results also are shown in FIG. 10. It will be seen by making a comparison with the sensor of Example 4 devoid of the porous body that the dependence of sensor output on NOx concentration was much greater when the oxygen pump electrode and NOx sensing electrode were made to contact each other via the porous body of alumina. It will also be appreciated that the dependence of sensor output on NOx concentration was made even greater when the porous film was obtained by supporting palladium on alumina.

Thus, by means of the nitrogen oxide sensor according to this aspect of the present invention, NO gas and $NO_2$ gas in particular among the nitrogen oxide gases in a measurement environment is oxidized and converted to $NO_2$ gas, peroxides of nitrogen of order greater than $NO_2$ and a mixture thereof, and a potential difference, based upon NOx concentration, across a sensing electrode and counter electrode is sensed to make possible the sensing of nitrogen oxide gas concentration. In addition, concentrations of nitrogen oxides can be sensed without interference from reducing gases such as hydrocarbon gas, typified by $C_3H_6$, and CO gas.

Another embodiment of the present invention will be described with reference to FIGS. 11 through 13.

Platinum and rhodium are used as NOx catalysts but an alloy thereof is not used as a potential difference sensing electrode (which exhibits activity to oxygen and NOx) per se. The present invention maintains that an electrode according to the invention is used in accordance with a principle different from that of the conventional concentration potential difference. That is, a mixed potential [the electrode potential (the potential difference with respect to the counter electrode) of the sensing electrode decided by NOx and $O_2$] decided by the simultaneous contribution of NOx and oxygen in the oxidation-reduction reaction of NOx (NO, $NO_2$), which is the reaction of the NOx sensing electrode, is used as an output. The construction of such a sensor is shown in FIGS. 11 and 12. So long as a sensing electrode 202 and counter electrode 203 (which is inactive to NOx) are placed on the same solid electrolytic substrate of zirconia, the arrangement of these electrodes is not particularly limited. It will suffice if oxygen is present in the environment of the sensing electrode and a mixed potential is formed. The opposing electrode 203 need only be insensitive to NOx under the conditions of use. Accordingly, the opposing electrode 203 usually is formed solely of platinum or zirconia is added to the platinum to adjust the electrode composition.

Figure 13:
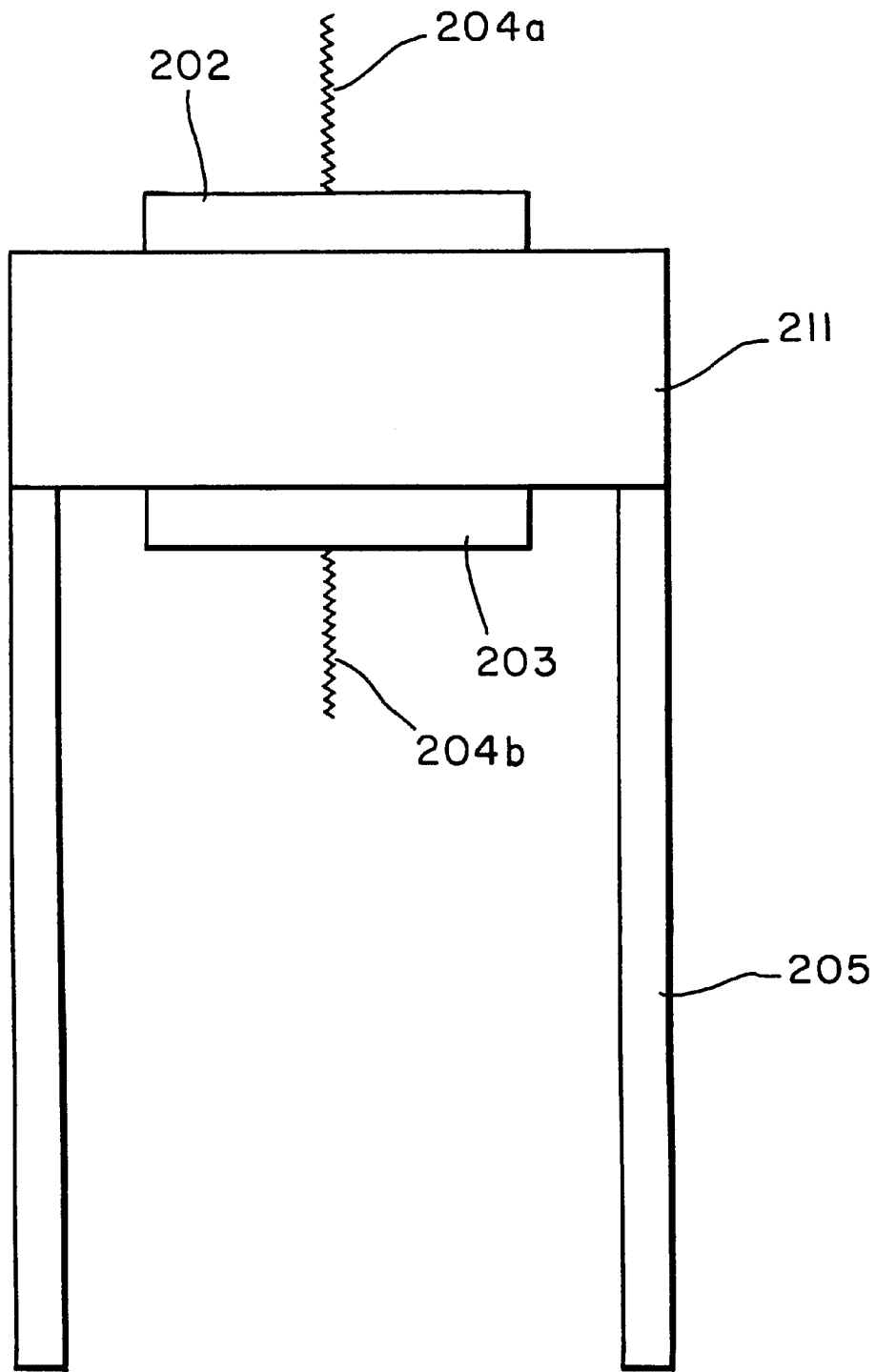
FIG. 13 is a front view showing an example of application using the electrodes of the present invention.

In the arrangement shown in FIG. 13, naturally the environment on the side of the counter electrode 203 naturally is made the atmosphere, by way of example.

In a case where NOx does not exist on the side of the counter electrode 203 in FIG. 13, an NOx-sensitive Pt—Rh alloy electrode according to the invention, for example, can be used and it should be obvious that this falls within the scope of the invention.

Figure 11:
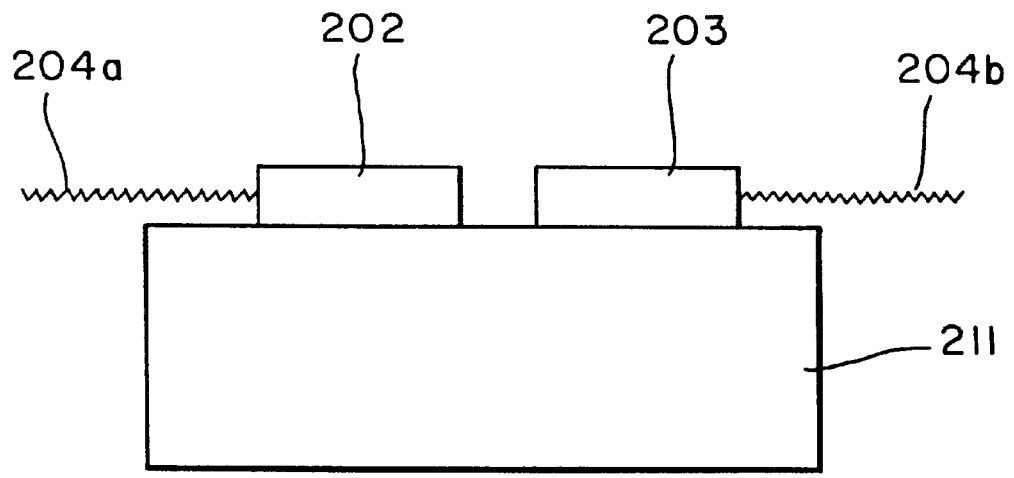
FIG. 11 is a front view showing an example of a basic element arrangement (co-planar) of electrodes according to the present invention.
Figure 12:
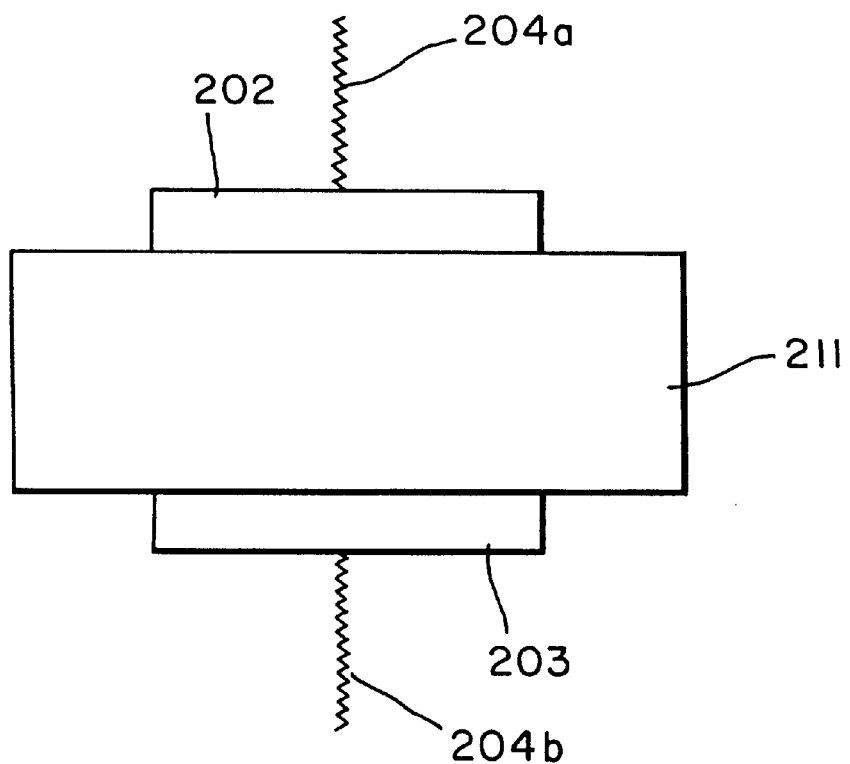
FIG. 12 is a front view showing an example of a basic element arrangement (top and bottom sides) of electrodes according to the present invention.

In FIGS. 11, 12 and 13, the electrodes 202, 203 have lead wires 204a, 204b, respectively, and a partition 205 isolates the counter electrode 203 from the gases sensed.

With an oxide electrode such as of $NiCr_2O_4$ reported heretofore, the conductivity of the electrode film per se is low under these conditions and it is necessary to form a collector under the electrode in order to capture the reaction charge. Since the electrode impedance of the oxide electrode per se is high, the electrode is susceptible to noise when it is used in an automotive vehicle, thus making it difficult to assure accuracy. Even if it is attempted to enlarge the electrode size, the fact that the electrode per se exhibits low conductivity means that a potential difference cannot be measured efficiently without a collector.

Though a noble-metal electrode has good conductivity, one that is capable of sensing NOx as a mixed potential is not available. Noble metals used heretofore in potential difference type NOx sensors have a catalyst property or are merely collectors, as set forth above. The present invention is based upon the idea of using a Pt—Rh alloy film in an NOx sensing electrode to achieve the oxygen adsorbing ability of the platinum and the catalytic ability of the added rhodium on the same electrode, and measuring the NOx potential difference that is due to the mixed potential. Accordingly, the alloy dispersion property of rhodium (the concentration of rhodium addition) and sensitivity of rhodium should have a correlation and, in fact, this is the result that has been obtained.

However, if a noble-metal electrode is active to oxygen per se and sensing is performed by the method of concentration potential difference using the structure shown in FIG. 13, for example, a fluctuation in oxygen concentration on the side of the sensing electrode 202 is sensed directly and it therefore becomes necessary to perform accurate control of the partial pressure of oxygen in the environment of the sensing electrode. In actuality this means nothing more than performing measurement by an oxygen concentration sensor in a region in which the oxygen concentration is in the vicinity of zero. In this region of oxygen concentration, output dependence upon oxygen concentration is extremely high and accurate control of concentration is essentially impossible.

By contrast, with mixed-potential type sensing according to the method of the invention, dependence upon oxygen concentration is very low and even very coarse control of oxygen concentration essentially has almost no effect upon NOx output. As a consequence, the Pt—Rh alloy electrode according to this scheme can actually be applied in environments inclusive even of automotive environments.

Figure 17:
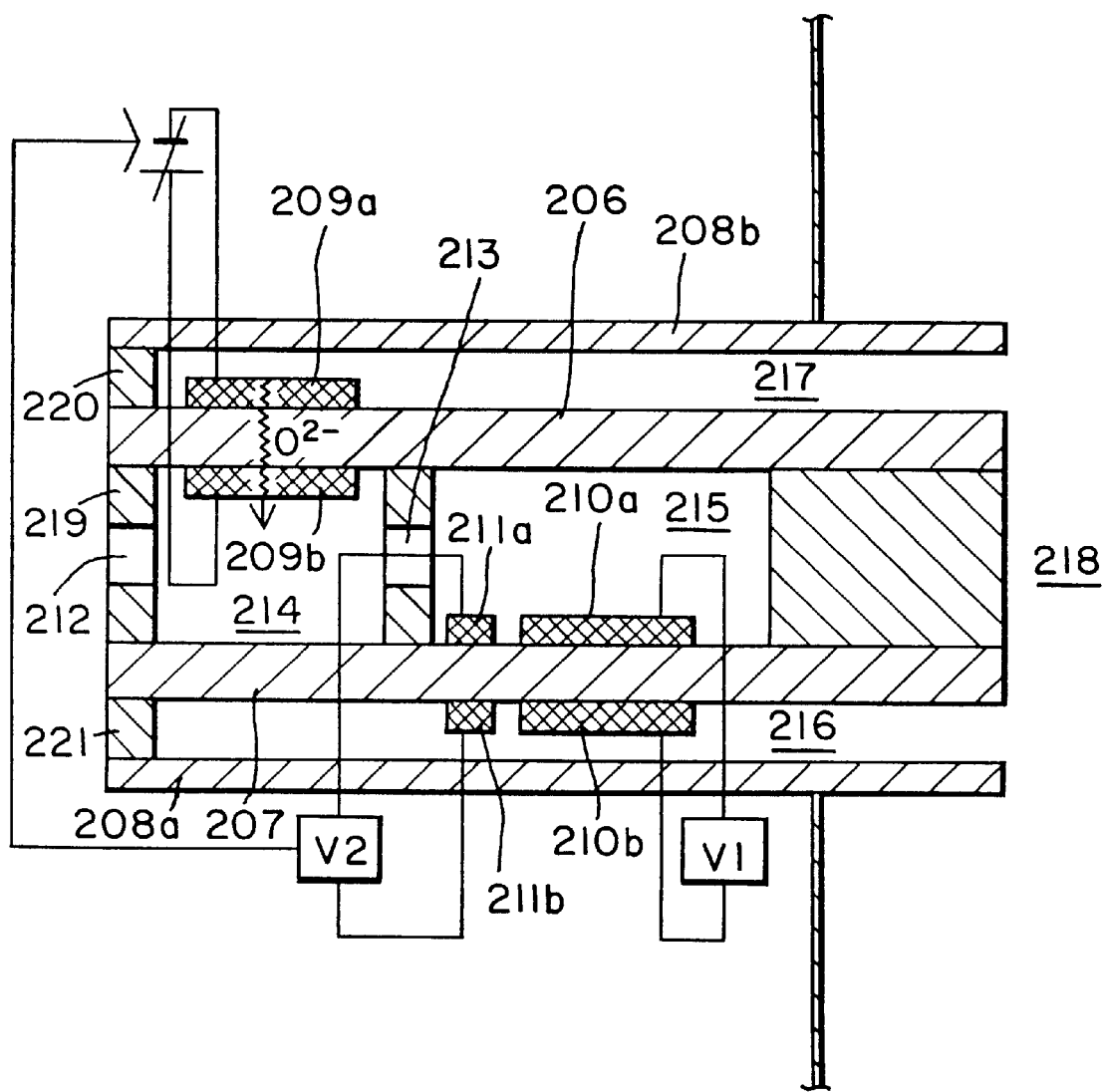
FIG. 17 is a sectional view showing an example of a total NOx sensor structure to which electrodes of the present invention are applied.
Figure 18:
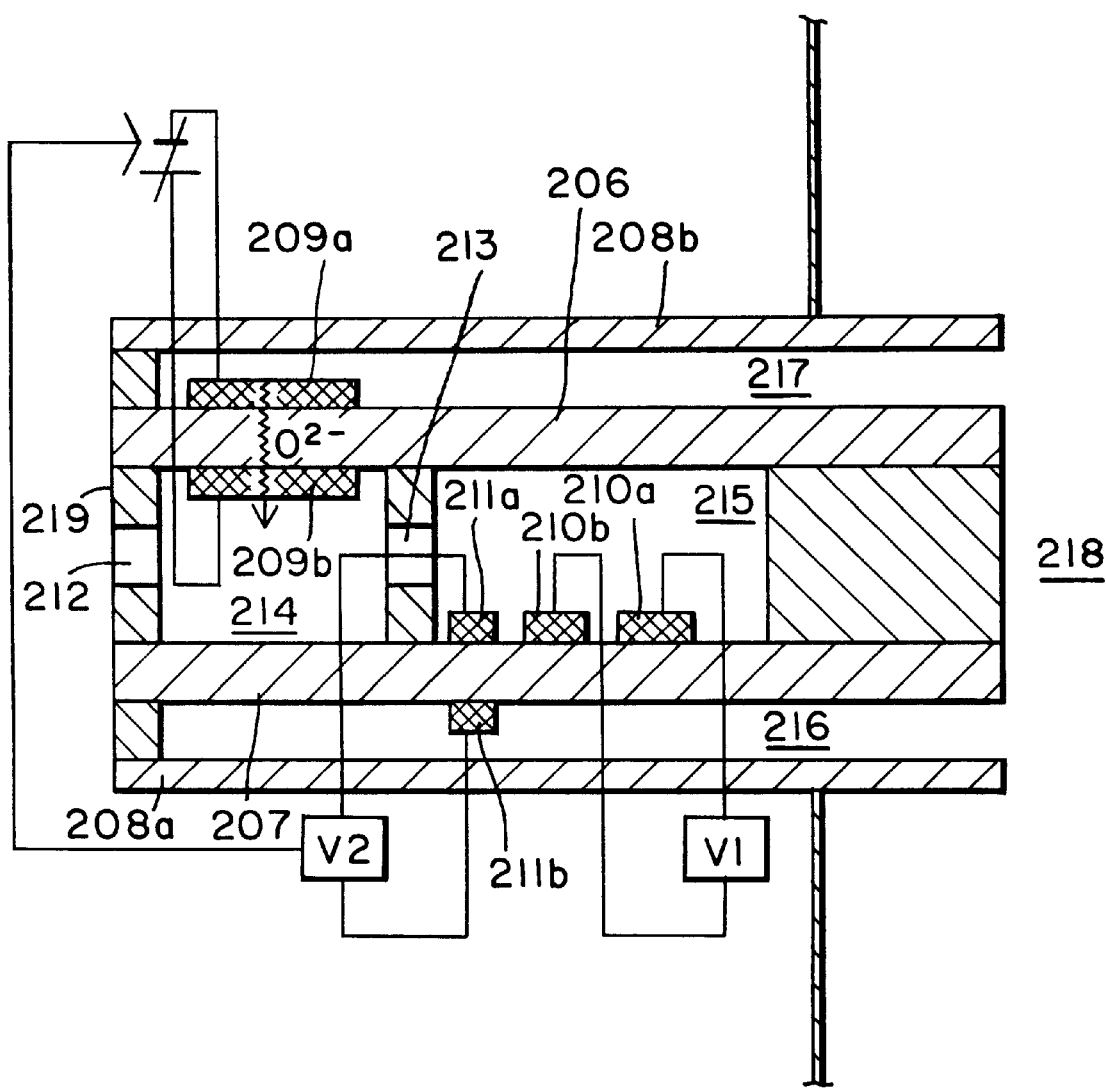
FIG. 18 is a sectional view showing another example of a total NOx sensor structure to which electrodes of the present invention are applied.

The structure of a sensor capable of sensing NO and $NO_2$ as total NOx in automotive exhaust gas is illustrated in FIGS. 17 and 18. The NO and $NO_2$ in exhaust gas is converted to a single gas component of either NO or $NO_2$ in a first chamber by means of an oxygen pumping electrode placed in the same chamber, potential difference sensing is performed in a second chamber by means of the electrode of the present invention. More specifically, in a case where NOx is sensed as $NO_2$, oxygen is pumped into the first chamber by the pumping electrode to oxidize the NO. Conversely, if NOx is sensed as NO by reduction of $NO_2$, the pumping voltage is reversed to discharge oxygen from the first chamber.

In any case, the oxygen concentration in the first chamber is subjected to feedback control by the oxygen sensor disposed in the second chamber. By incorporating the above-described mixed potential sensing technique in the sensor structure depicted in FIGS. 17 and 18, the high dependence upon the partial pressure of oxygen possessed heretofore by the noble-metal electrode per se is largely mitigated so that such an electrode may be used in an automotive sensor capable of sensing total NOx.

The well-known solid electrolytic substrate of zirconia is used. The method of forming the electrode for this invention generally in the screen printing method. The screen printing method is capable of using a green sheet as the substrate on which printing is performed. Though it is possible to use a sintered substrate as a matter of course, using a green sheet is extremely advantageous in that any shape can be obtained and complicated layered structures can be formed in simple fashion. In addition, adhesion to oxide electrodes is much higher than when a sintered substrate is used. It should be noted, however, that the present invention is not especially limited to a green sheet.

Furthermore, the invention is not limited to a forming method based screen printing. Methods which may be used include thin-film sputtering, coating with a colloidal solution, etc.

An alloy electrode material comprising platinum and rhodium alloy or a cermet electrode material comprising platinum-rhodium alloy and zirconia is used in the form of a paste obtained by kneading powders of these materials together with an organic binder such as PVA, a solvent thereof and a dispersant. The paste is applied by the screen printing method. Individual powders of the platinum and rhodium or alloy powder thereof may be used. If a mixed paste of platinum powder and rhodium powder is sintered at a high temperature of 1200° C. or more, complete alloying takes place. The reason for this is that it is required to sinter the zirconia green sheet at a temperature of 1300° C. or greater.

With regard to a method of adding zirconia to platinum and rhodium, the powder of the material is obtained by co-precipitation in a system in which an aqueous solution of zirconic acid, for example, has been directly added to an aqueous solution of platinic acid (the same is true for an aqueous solution of rhodium).

A material obtained by adding $Y_2O_3$ to zirconia at the same time and providing this with ion conductivity is fabricated in the same manner. The addition of zirconia is effective in order to control the sintered composition of the electrode. The amount of zirconia added is adjusted in conformity with the amount of sintering shrinkage of the green sheet of zirconia and the desired electrode composition. In general, 1–2 wt % is added with respect to the electrode metal component, and an amount of 5–15 wt % is preferred in terms of the electrode composition.

Forming the Pt—Rh electrode of the present invention in a sensor substrate obtained by stacking and sintering green sheets of zirconia is easy and is very effective in improving the NOx sensitivity characteristic. For example, it is effective to use a zirconia sheet of high ionic conductivity, to which 8 mol % of $Y_2O_3$ has been added, as the sensor substrate. In an actual sensor, the amount of added $Y_2O_3$ in the zirconia green sheet is decided based upon both the substrate strength characteristic and long-term stability. In other words, a $Y_2O_3$ composition that will not cause problems in terms of long-term stability, such as one that will not cause crystal transformation and that exhibits a high strength, is desired.

Detailed examples will now be described.

EXAMPLE 7

Basic method of fabrication and characteristics according to the invention:

A sensor sample having the structure shown in FIG. 1 was fabricated using a green sheet 211 of zirconia, to which 8 mol % of $Y_2O_3$ had been added, as a oxygen ion conductor. The green sheet was fabricated to a thickness of 0.3 mm by a method using a doctor blade and was cut to a sample size of 4 mm×6 mm. A paste obtained by adding prescribed amounts of organic binder and an organic solvent to a Pt—Rh alloy powder and kneading them together was fabricated as the material of the sensing electrode 202. The amount of rhodium added was 5 wt % with respect to the total amount of platinum and rhodium. Zirconia was added to the paste to adjust the electrode porosity. To obtain the counter electrode 203, platinum paste was printed on the surface of the zirconia sheet 211 so as to form an electrode pair with the sensing electrode 202. Zirconia was added to the paste in dispersed fashion to adjust the electrode composition in the same manner as the sensing electrode 202.

Figure 14:
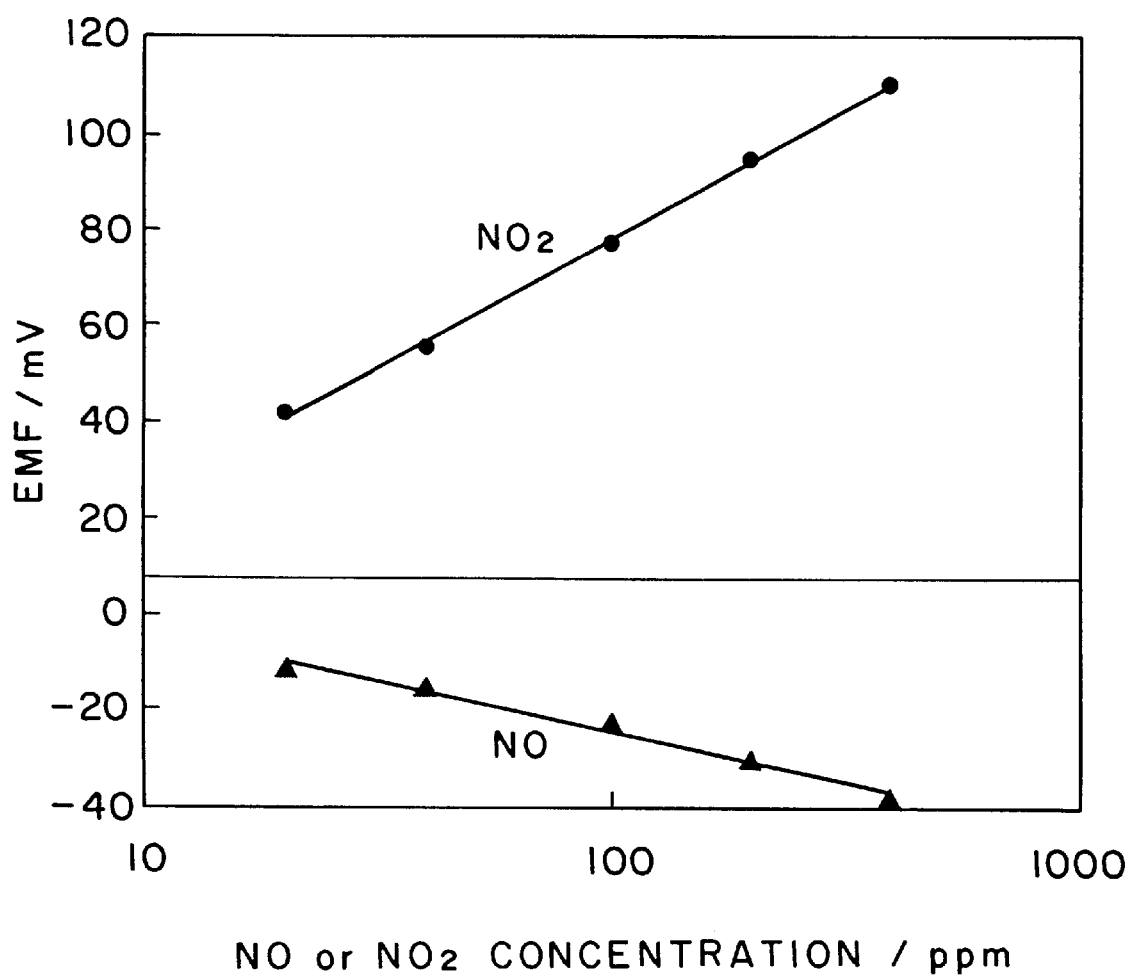
FIG. 14 is a graph showing an element output characteristic (NOx concentration dependence) of a Pt—Rh (5%) electrode according to the present invention.

The green sample thus fabricated was sintered at 1400° C., the lead wires 204a, 204b were attached to the electrodes 202, 203, respectively, and the sample was then evaluated in regard to sensitivity to NO and $NO_2$ gas. In order to evaluate sensitivity to these gases, a quartz tube was placed in an electric oven, the sample was inserted into the quartz tube and the potential difference across the sensing electrode 202 and counter electrode 203 was measured while the measurement gas was passed through the tube. The measurement gas was measured every five liters of total flow quantity while adding 4% $O_2$ and 50 ppm of NO or $NO_2$ to an $N_2$ base. The measurement temperature was regulated by controlling the electric oven using a thermocouple provided in the vicinity of the sensor sample. The temperature of the environment obtained was 600° C. The dependence of the sensor output upon the concentration of NOx is shown for $NO_2$ and NO in FIG. 14. It will be appreciated from these results that the sensitivity to $NO_2$ indicates an equivalent or higher output in comparison with the $NiCr_2O_4$ sensing electrode reported in the prior art. The electrode is sensitive to NO as well.

EXAMPLE 8

Figure 15:
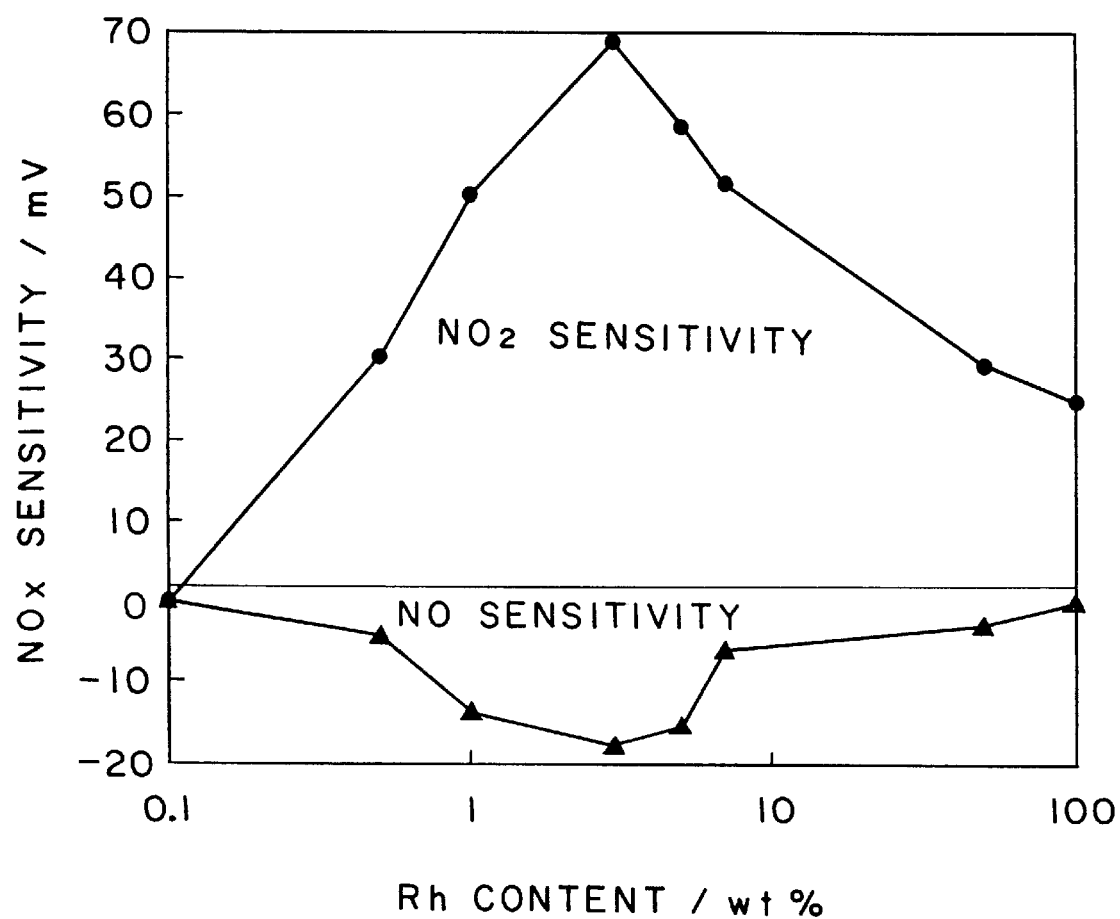
FIG. 15 is a graph illustrating the dependence of NO, $NO_2$ sensitivities on Rh composition in the case of electrodes according to the present invention.

Sensor samples fabricated in the same manner as set forth in Example 7 were prepared but the proportion of rhodium in the samples was varied. The adjustment of the proportions of platinum and rhodium in the compositions was performed using mixed powders of platinum and rhodium. The percentages of rhodium in the composition were 0.1%, 0.5%, 1.0%, 3.0%, 5.0%, 7.0%, 50% and 100% with respect to the total quantity of platinum and rhodium. Measurement of sensitivity was performed using an apparatus similar to that described in Example 7, and sensitivity to NO (50 ppm) or $NO_2$ (50 ppm) was evaluated every five liters of total gas flow at an environment temperature of 600° C. The results are shown in Table 3 and in FIG. 15. It will be understood from these results that a high sensitivity to $NO_2$ was obtained at a rhodium ratio of 0.5% or greater. It will also be appreciated that sensitivity to NO was obtained at rhodium ratios of more than 0.5% and less than 50%.

TABLE 3

| Rh COMPOSITION RATIO (wt %) | NO SENSITIVITY (mV) | $NO_2$ SENSITIVITY (mV) |
| --- | --- | --- |
| 0.1 | −0.1 | 0.8 |
| 0.5 | −4.3 | 30.3 |
| 1.0 | −13.6 | 50.2 |
| 3.0 | −17.9 | 68.8 |
| 5.0 | −15.4 | 58.5 |
| 7.0 | −6.0 | 51.5 |
| 50 | −3.0 | 29.4 |
| 100 | −0.1 | 24.7 |

EXAMPLE 8

A sample was fabricated in a manner similar to that described in Example 7. In this example, however, the sample was assembled into the structures shown in FIGS. 17 and 18 after electrodes were printed on the zirconia green sheet.

A spacer 219 having a first inlet for measurement gas and a second inlet opposing this inlet and spaced away therefrom is interposed between a solid electrolytic substrate 206 for oxygen pumping and an opposing solid electrolytic substrate 207 for an Nox sensor and oxygen sensor, thereby forming a first chamber 214 and a second chamber 215. The substrate 206 has oxygen pumping electrodes 209a, 209b on its top and bottom surfaces on the side of the first chamber 214. The substrate 207 has an NOx sensing electrode 210a and its counter electrode 210b on its top and bottom surfaces, respectively, as well as an oxygen sensing electrode 211a and its opposing electrode 211b on its top and bottom surfaces, respectively. The oxygen electrode 209b is exposed to the interior of the first chamber 214, and the NOx sensing electrode 210a and oxygen sensing electrode 211a are exposed to the interior of the second chamber 215.

In the example of FIG. 18, the oxygen sensing electrode 211a and its counter electrode 211b are both exposed to the interior of the second chamber 215, but in other respects this arrangement is the same as that of the example shown in FIG. 17.

A partition 208b of a reference environment duct for the NOx sensor and oxygen sensor is arranged to oppose the substrate 206 via a spacer 220, thereby forming an oxygen inlet duct 217 for oxygen pumping. Further, a partition 208a of an oxygen inlet duct for oxygen pumping is arranged to oppose the substrate 207 via a spacer 221, thereby forming a reference environment duct 216 for the NOx sensor and oxygen sensor. The ducts 216, 217 communicate with the reference environment (the atmosphere). The ducts 216, 217 are effective as the oxygen pumping duct.

A potential difference V1 across the NOx sensing electrode 210a and the NOx counter electrode is measured, as well as a potential difference V2 across the oxygen pumping electrodes 209a, 209b and the oxygen sensing electrode 211a and its counter electrode 211b.

In the sensor structure of the examples shown in FIGS. 17 and 18, the concentration of oxygen in the exhaust gas introduced to the first chamber 214 was adjusted by the pumping electrodes 209a, 209b to obtain a single component gas of NOx. The NOx converted to the single gas of NO or $NO_2$ was sensed as a potential difference by the Pt—Rh (5%) electrodes 210a, 210b in the second chamber 215. The oxygen concentration in the second chamber 215 was set to a prescribed concentration region by the pumping electrodes 211a, 211b. The concentration of NO or $NO_2$ was sensed as the single output $V_1$ by the inventive electrodes 210a, 210b formed in the second chamber 215. The total NOx output characteristic was evaluated in a mixed gas of NO (25 ppm) and $NO_2$ (25 ppm) in the case of the $NO_2$ sensing method and in the case of the NO sensing method when the oxygen concentration in the second chamber 215 was set to a range of concentrations of from 4% to 50%.

Figure 16:
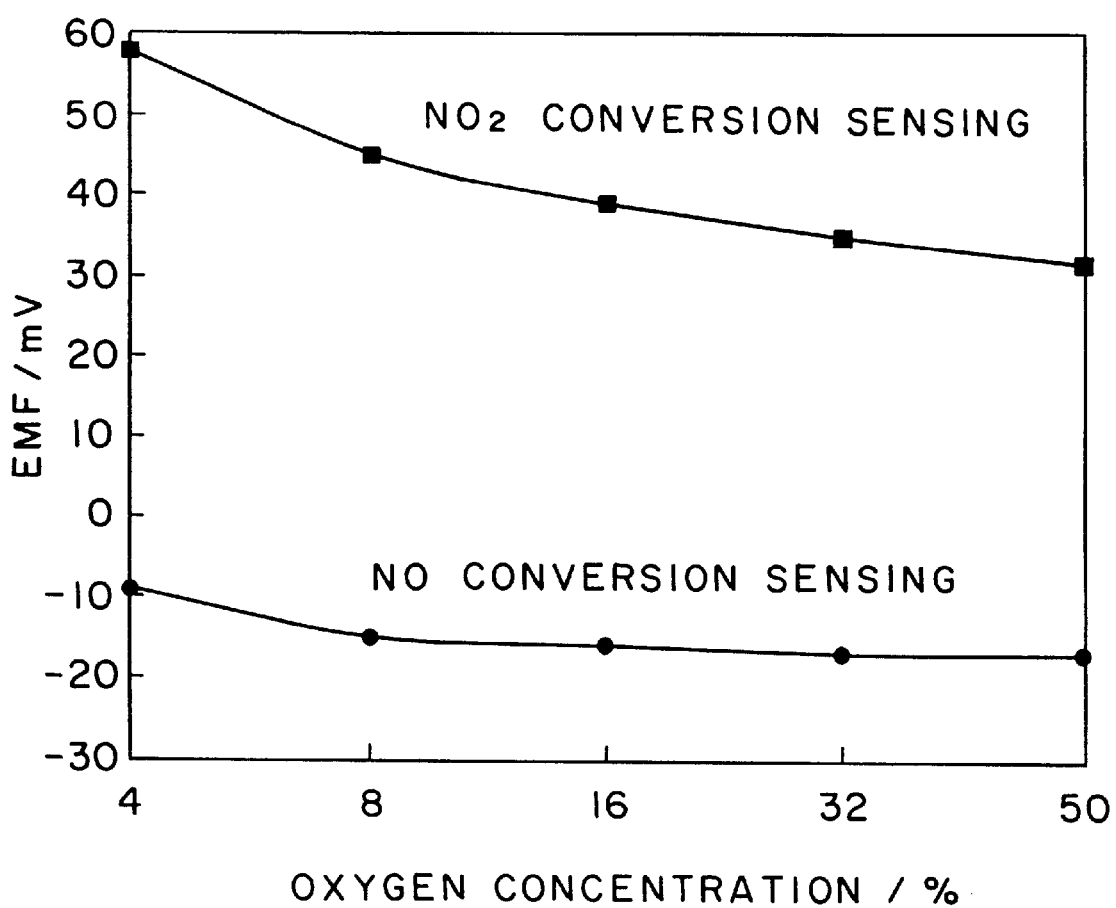
FIG. 16 is a graph showing dependence on oxygen concentration in a total NOx sensor structure.

It will be understood from the results of FIG. 16 that making joint use of the inventive electrodes in the sensor structure of the kind shown in these examples makes it possible to sense NOx (NO and $NO_2$) in exhaust gas as total NOx concentration, eliminates the high oxygen of the Pt—Rh sensing electrode itself and allows stabilized sensing of NOx to be carried out. In other words, with the $NO_2$ sensing scheme, an accuracy of ±2.5 ppm can be acquired in terms of sensitivity in the low concentration region of NOx (50 ppm) even with coarse control (±1% in terms of oxygen concentration) in the neighborhood of 4% oxygen, which is the highest oxygen concentration dependence in the range of measurement. With the NO sensing scheme, output is substantially saturated in the region of high oxygen concentration. No particular problems arise if oxygen concentration can be kept above 10%.

The present invention has the following effects taking into consideration conditions in which the invention is used in an ordinary room to conditions in which the invention is used in automotive exhaust gas:

(1) In an arrangement in which NOx concentration is measured based upon potential difference, a very large detection output not achieved with the conventional noble-metal electrodes could be obtained by using the inventive Pt—Rh alloy electrode or a cermet electrode consisting of platinum, rhodium and zirconia. The result was improved accuracy of NOx concentration measurement.

(2) Using the Pt—Rh alloy electrode or the cermet electrode consisting of platinum, rhodium and zirconia improved the conductivity of the electrode per se and made it unnecessary to form a collector on the sensing electrode.

(3) The method of integrating and sintering green sheets of zirconia eliminated problems of electrode material evaporation and poor adhesion seen with conventional oxide electrode materials.

(4) Placing the inventive electrodes in a chamber in which oxygen concentration is controlled to a certain extent greatly reduces the dependence of the electrode itself on the partial pressure of oxygen. This improves measurement accuracy by a wide margin when the sensor is actually driven.

As many apparently widely different embodiments of the present invention can be made without departing from the spirit and scope thereof, it is to be understood that the invention is not limited to the specific embodiments thereof except as defined in the appended claims.

What is claimed is:

1. A nitrogen oxide sensor comprising:

first and second solid electrolytic substrates exhibiting oxygen ion conductivity and defining a measurement chamber;

a noble-metal reference electrode, which is active only to oxygen, formed on one side of said first solid electrolytic substrate;

an NOx sensing electrode, which is at least active to NOx and oxygen, formed on the opposite side of said first solid electrolytic substrate within said measurement chamber, a potential difference across said sensing electrode and said reference electrode being output as a signal indicative of NOx concentration; and means for converting nitrogen oxides in a gas to be examined or measured gas to $NO_2$ and to peroxides of nitrogen and formed within said measurement chamber, after which the nitrogen oxides in the gas to be examined or measured gas are sensed by said sensing electrode as the peroxides of nitrogen or as a mixed gas of $NO_2$ and said peroxides of nitrogen.

2. The sensor according to claim 1, wherein the means for converting nitrogen oxides comprises an NOx converting electrode formed within said measurement chamber on said second solid electrolytic substrate, said NOx converting electrode having the ability to oxidize nitrogen oxides in the gas to be examined or measured gas to $NO_2$ and peroxide compounds of nitrogen having an oxidation order greater than that of $NO_2$, said sensor further comprising a counter electrode of said NOx converting electrode opposed to said NOx converting electrode through said second solid electrolytic substrate, wherein the nitrogen oxides in the gas to be examined or measured gas are converted to $NO_2$ and to peroxides of nitrogen by said NOx converting electrode.

3. The sensor according to claim 2, further comprising an oxygen sensing electrode disposed in said measurement chamber and an oxygen pumping electrode disposed in said measurement chamber for adjusting oxygen concentration, wherein a current applied to said oxygen pumping electrode is controlled using an output signal from said oxygen sensing electrode.

4. The sensor according to claim 3, wherein a porous protective film having heat resistance and an oxidation catalyst ability is formed at least on the NOx sensing electrode or the oxygen pumping electrode and the NOx sensing electrode.

5. The sensor according to claim 3, further comprising an auxiliary pumping portion for controlling oxygen concentration at said NOx sensing electrode; and wherein a driving voltage applied to said auxiliary pumping portion is controlled based upon the oxygen concentration sensed by said oxygen sensing electrode.

6. The sensor according to claim 5, wherein an oxidation catalyst for oxidizing nitrogen oxide gases is formed between said oxygen pumping electrode and said NOx sensing electrode.

7. The sensor according to claim 5, wherein (1) (a) one of the oxygen pumping electrode or an electrode of the auxiliary oxygen pumping portion and (b) the NOx sensing electrode or (2) both the Nox sensing electrode and said reference electrode are disposed in said measurement chamber, and a gas diffusion inlet is provided in said chamber.

8. The sensor according to claim 7, wherein said oxygen pumping electrode and at least the NOx sensing electrode are disposed with their electrode surfaces opposing each other in the chamber.

9. The sensor according to claim 8, wherein a space between said oxygen pumping electrode and at least the NOx sensing electrode is filled with a porous body.

10. The sensor according to claim 9, wherein the porous body filling the space between said oxygen pumping electrode and at least the NOx sensing electrode has a high degree of electrical insulation.

11. The sensor according to claim 1, further comprising a heater provided on at least one of said first and second solid electrolytic substrates for controlling the temperature of said sensor.

12. The sensor according to claim 11, wherein the NOx sensing electrode produces a mixed potential owing to concurrent electrochemical reactions with oxygen and NOx at the NOx sensing electrode, and a potential difference based upon total NOx gas concentration between the NOx sensing electrode and its counter electrode is measured.

13. The sensor according to claim 1, wherein said NOx sensing electrode is an alloy electrode comprising platinum and rhodium or is a cermet electrode comprising a platinum-rhodium alloy and zirconia.

* * * * *